United States Patent
Craige et al.

(10) Patent No.: US 10,704,003 B2
(45) Date of Patent: Jul. 7, 2020

(54) OIL-IN-WATER EMULSIONS

(71) Applicants: Quadrise International Ltd, London (GB); Akzo Nobel Chemicals International B.V., Arnhem (NL)

(72) Inventors: Simon Craige, Kalundborg (DK); Jason Victor Miles, London (GB); Dennis Selse, Myggenas (SE); Joakim Krigsman, Sater (SE)

(73) Assignees: QUADRISE INTERNATIONAL LIMITED (GB); NOURYON CHEMICALS INTERNATIONAL B.V. (NL)

(*) Notice: Subject to any disclaimer, the term of this patent is extended or adjusted under 35 U.S.C. 154(b) by 0 days.

(21) Appl. No.: 15/773,351

(22) PCT Filed: Nov. 3, 2016

(86) PCT No.: PCT/GB2016/053413
§ 371 (c)(1),
(2) Date: May 3, 2018

(87) PCT Pub. No.: WO2017/077302
PCT Pub. Date: May 11, 2017

(65) Prior Publication Data
US 2018/0320096 A1    Nov. 8, 2018

(30) Foreign Application Priority Data

Nov. 6, 2015 (GB) .................................. 1519615.7
May 23, 2016 (GB) .................................. 1609042.5

(51) Int. Cl.
*C10L 1/32* (2006.01)
*C10L 1/238* (2006.01)
(Continued)

(52) U.S. Cl.
CPC .......... *C10L 1/328* (2013.01); *B01F 17/0042* (2013.01); *C08L 95/005* (2013.01);
(Continued)

(58) Field of Classification Search
CPC .. B01F 17/0042; C08L 95/005; C10L 1/1817; C10L 1/188; C10L 1/198;
(Continued)

(56) References Cited

U.S. PATENT DOCUMENTS 3,630,953 A    12/1971  Simon Ralph et al.
4,746,460 A    5/1988   Taylor
(Continued)

FOREIGN PATENT DOCUMENTS

CN    1152607    6/1997
EP    0512721    11/1992
(Continued)

OTHER PUBLICATIONS

Machine Translation and English abstract of JP08277396.
(Continued)

*Primary Examiner* — Cephia D Toomer
*Assistant Examiner* — Chantel L Graham
(74) *Attorney, Agent, or Firm* — Bell & Manning, LLC

(57) ABSTRACT

The invention relates to an oil-in-water emulsion comprising an oil phase and an aqueous phase, and a primary surfactant, wherein the oil phase is dispersed in the aqueous phase, and wherein the oil-in-water emulsion has: an average droplet size distribution (D[4,3]) in the range of from 3 to 15 um and less than 3 wt % of the droplets have a particle size of greater than 125 um; a viscosity of greater than 100 and up to 700 mPas at 50° C.+−10% and 20 s$^{-1}$+−10%; and a static stability of less than 5% residue after centrifugation at 50° C.+−10% and 2000 g=10% for 30 minutes+−10%.

14 Claims, 15 Drawing Sheets

(51) Int. Cl.
*C10L 1/222* (2006.01)
*C10L 1/198* (2006.01)
*G01N 33/18* (2006.01)
*C08L 95/00* (2006.01)
*B01F 17/00* (2006.01)
*C10L 1/18* (2006.01)
*C10L 1/22* (2006.01)
*C10L 1/188* (2006.01)

(52) U.S. Cl.
CPC .............. *C10L 1/198* (2013.01); *C10L 1/2222* (2013.01); *C10L 1/238* (2013.01); *G01N 33/1833* (2013.01); *C10L 1/188* (2013.01); *C10L 1/1817* (2013.01); *C10L 1/221* (2013.01); *C10L 1/2225* (2013.01); *C10L 2200/0453* (2013.01); *C10L 2230/14* (2013.01); *C10L 2250/06* (2013.01); *C10L 2250/082* (2013.01); *C10L 2270/026* (2013.01)

(58) Field of Classification Search
CPC ...... C10L 1/221; C10L 1/2222; C10L 1/2225; C10L 1/238; C10L 1/328; C10L 2200/0453; C10L 2230/14; C10L 2250/06; C10L 2250/082; C10L 2270/026; G01N 33/1833
See application file for complete search history.

(56) References Cited

U.S. PATENT DOCUMENTS

| | | |
|---|---|---|
| 4,776,977 A | 10/1988 | Taylor |
| 4,934,398 A | 6/1990 | Chirinos et al. |
| 5,354,504 A | 10/1994 | Rivas et al. |
| 5,399,293 A | 3/1995 | Nunez et al. |
| 5,505,876 A | 4/1996 | Rivas et al. |
| 5,863,301 A | 1/1999 | Grosso et al. |
| 5,879,419 A | 3/1999 | Moriyama et al. |
| 6,113,659 A | 9/2000 | Logaraj et al. |
| 7,763,664 B2 | 7/2010 | Bonn et al. |
| 2010/0314296 A1 | 12/2010 | Pacheco et al. |
| 2013/0118598 A1 | 5/2013 | Gutierrez et al. |
| 2015/0184063 A1 | 7/2015 | Gutierrez et al. |

FOREIGN PATENT DOCUMENTS

| | | | |
|---|---|---|---|
| EP | 0808889 | | 11/1997 |
| EP | 1935969 | | 6/2008 |
| FR | 2869242 | | 10/2005 |
| GB | 2270323 | | 3/1994 |
| GB | 2295972 | | 6/1996 |
| JP | 08277396 | | 10/1996 |
| JP | 2003327979 | | 11/2003 |
| RU | 2021329 | C1 | 10/1994 |
| RU | 2422192 | C2 | 6/2011 |
| RU | 2542048 | C2 | 2/2015 |
| WO | WO9307238 | | 4/1993 |
| WO | WO9963025 | | 12/1999 |
| WO | WO0078901 | | 12/2000 |
| WO | WO2007/112967 A1 | | 10/2007 |
| WO | WO2009087199 | | 7/2009 |
| WO | WO2010086619 | | 8/2010 |
| WO | WO-2010086619 A1 * | | 8/2010 .............. C10L 1/328 |
| WO | WO2010/129951 A1 | | 11/2010 |

OTHER PUBLICATIONS

International Search Report and Written Opinion mailed in PCT/GB2016/053413, dated May 9, 2017.

Poteau et al., Influence of pH on stability and dynamic properites of asphaltenes and other amphiphilic molecules at the oil-water interface, Energy & Fuels, American Chemical Society, vol. 19, No. 4, Mar. 18, 2005, pp. 1337-1341.

Jing et al., Dynamic Stability of Heavy Crude Oil-in-Water Emulsions, Journal of Dispersion Science and Technology, vol. 37, No. 7, Aug. 12, 2015, pp. 980-990.

GB Search Report mailed in GB1519615.7, dated Apr. 28, 2016.

* cited by examiner

OIL-IN-WATER EMULSIONS

CROSS-REFERENCE TO RELATED APPLICATIONS

The present application is a National Stage Entry of International Application No. PCT/GB2016/053413 that was filed Nov. 3, 2016, the entire contents of which are hereby incorporated by reference, which claims priority to GB Patent Application No. 1519615.7 that was filed Nov. 6, 2015 and GB Patent Application No. 1609042.5 that was filed May 23, 2016, the entire contents of each of which are hereby incorporated by reference.

TECHNICAL FIELD

This invention relates to oil-in-water (water continuous) emulsions that can be used as fuels, and which have high static and dynamic stability. The invention also relates to a process for their preparation. The invention further relates to methods for measuring dynamic stability and static stability of oil-in-water emulsions.

BACKGROUND

Significant changes in the range and use of primary fossil fuels throughout the world over the last years have influenced and altered the way that energy intensive industries source their requirements and operate. These industrial trends have been significantly affected by fuel economics, diversification and availability, as well as by an increasing need to improve environmental performance. Higher prices have resulted in a move away from conventional oil based fuels towards cheaper alternatives with reduced environmental impact. Although feasible primary energy alternatives to oil exist for land-based industries, the shipping market remains predominantly dependent on oil-based products, particularly heavy fuel oil-based products, and is likely to do so for the foreseeable future.

Heavy fuel oils are normally produced by blending viscous refinery residues with higher value distillate fuels to provide the lower viscosity characteristics required for acceptable fuel handling and combustion performance. Direct use of high viscosity refinery residues requires high-temperature storage and handling that limits and complicates their potential use, and consequently lowers their value. As an alternative to blending refinery residues for fuel oil production, further processing (e.g. coking, hydrocracking, etc.) of the residue can be applied at the refinery to yield additional distillate fuels. However this strategy requires large capital investments to be made by the oil refinery, produces some lower value products, generates difficult to market by-products, results in an increase of emissions (including greenhouse and acid gases), all of which can serve to limit the economic advantage of this approach.

Preparation of emulsion fuels has been previously described, for example in Logaraj et al; "Emulsification—A solution to Asphaltene Handling Problems", presented at the ISSA/AEMA $2^{nd}$ Joint Conference, Mar. 12-13, 2000, Amelia Island, Florida, GB 2 475 090, U.S. Pat. Nos. 4,776,977, 5,419,852, 5,603,864, 6,530,965 B2, US 2010/0043277 A, U.S. Pat. Nos. 5,411,558, 5,360,458, 5,437,693, 5,976,200 and 6,113,659. Droplet size distribution characteristics of an emulsion fuel and the resulting combustion performance has been previously described in WO 2008/074138, EP 1 935 969 and U.S. Pat. No. 5,603,864. WO 2014/082981 describes Bitumen emulsions, and U.S. Pat. No. 6,194,472 describes colloidal dispersions of hydrocarbons in water, in which softening point of the hydrocarbons in the dispersion exceeds about 95° C.

There remains a need for an oil-in-water emulsion, particularly an oil-in-water emulsion fuel, and more particularly a marine fuel, that has improved stability during storage and handling.

SUMMARY OF INVENTION

The present invention is directed to an oil-in-water emulsion, particularly a fuel, and a method for its production, whereby the distillates conventionally used for blending down hydrocarbon residue viscosity are not required, and are replaced with water and a small amount of stabilising chemical additives. The invention can be directly applied to a wide range of heavy hydrocarbon and refinery residue streams. Such hydrocarbon-containing materials include: atmospheric and vacuum residues, visbroken or thermally cracked residues, vacuum flashed visbroken residues, and other heavy, viscous residues produced from refinery and/or heavy oil upgrading facilities (such as hydrocracking, de-asphalting and similar conversion processes).

An added benefit of the invention is to provide a means of enhancing the handling and combustion characteristics by emulsification. Although the importance of the droplet size distribution characteristics of an emulsion fuel on its resulting combustion performance has been previously documented (see above), there remains a need to simultaneously control rheological properties in order to produce a fuel that can be handled in a wide range of system applications. For a diesel engine application, for example in a ship's engine system, the rheological properties of the fuel are important in ensuring sustainable hydraulic performance of the fuel handling and injection systems. In the present invention, the droplet size distribution of the oil-in-water emulsion is maintained within particular limits. When used as a fuel, this enables control of both the rheological characteristics during the fuel handling, and the (rapid) burn-out of the fuel to ensure acceptable (if not complete) carbon utilisation in terms of efficiency and resulting emissions.

For an oil-in-water emulsion to be used successfully as a fuel, for example as a marine fuel, it must be robust to both storage (static) stability and handling (dynamic) stability. Although preparation of emulsion fuels has been previously described in some of the documents mentioned above, the stability requirements for their subsequent use have not been established.

Accordingly, a first aspect of the invention provides an oil-in-water emulsion comprising an oil phase and an aqueous phase, and a primary surfactant, wherein the oil phase is dispersed in the aqueous phase, and wherein the oil-in-water emulsion has the following characteristics:

an average droplet size (D[4,3]) in the range of from 3 to 15 μm;

less than 3 wt % of the droplets have a particle size of greater than 125 μm;

a viscosity of greater than 100 and up to 700 mPas at 50° C. (±10%) and 20 $s^{-1}$ (±10%);

a static stability of less than 5% residue after centrifugation at 50° C. (±10%) and 2000 g (±10%) for 30 minutes (±10%);

An emulsion having the above characteristics can have a dynamic stability of less than 0.30 μm increase in mean (D[4,3]) droplet size per minute at 50° C. (±10%).

A second aspect of the invention provides an oil-in-water emulsion comprising an oil phase and an aqueous phase, and a primary surfactant, wherein the oil phase is dispersed in the aqueous phase, in which the primary surfactant is selected from one or more from the group consisting of fatty alkyl amines, ethoxylated fatty alkylamines, ethoxylated fatty alkyl monoamines, methylated fatty alkyl monoamines, methylated fatty alkyl amines, and quaternary fatty alkyl amines; and wherein the oil-in-water emulsion has the following characteristics:

an average droplet size (D[4,3]) in the range of from 3 to 15 μm;
less than 3 wt % of the droplets have a particle size of greater than 125 μm; and
a viscosity of greater than 100 and up to 700 mPas at 50° C.±10% and 20 $s^{-1}$±10%.

An emulsion having such characteristics can result in high static and dynamic stability, as set out above.

In a third aspect the invention provides a process for preparing the oil-in-water emulsion fuel comprising the steps of:

heating a hydrocarbon-containing oil;
mixing water and one or more chemical additives to form an aqueous solution; and
blending the hydrocarbon residue and the aqueous solution under conditions sufficient to form an oil-in-water emulsion having the above characteristics.

In a fourth aspect the invention provides for a method for determining the static stability of an oil-in-water emulsion comprising the steps of:

providing an oil-in-water emulsion;
centrifuging the oil-in-water emulsion under predetermined conditions for a pre-determined period of time;
determining the amount of residue deposited from the oil-in-water emulsion after the pre-determined period of time; and
determining the oil-in-water emulsion's static stability.

In a fifth aspect the invention provides a method for determining the dynamic stability of an oil-in-water emulsion comprising the steps of:

providing an oil-in-water emulsion;
recirculating the oil-in-water emulsion in a recirculation loop; and
analysing the oil-in-water emulsion at a first time before recirculation, and at a predetermined time after recirculation; and
comparing the samples taken to determine the oil-in-water emulsion's dynamic stability.

Values of parameters are sometimes expressed in terms of a particular value±a percentage. This means that the value of that parameter can be either the value specified, or a range of values either side of the specified value, calculated from the percentage. For example, a viscosity of greater than 100 and up to 700 mPas at 50° C. (±10%) and 20 $s^{-1}$ (±10%) is referred to above. This means that the viscosity is greater than 100 and up to 700 mPas, at a temperature that is either 50° C., or in the range of from 45 to 55° C., and at a shear rate that is either 20 $s^{-1}$, or in the range of from 18-22 $s^{-1}$. Similarly, a static stability of less than 5% residue after centrifugation at 50° C. (±10%) and 2000 g (±10%) for 30 minutes (±10%) means that the static stability is such that less than 5% residue (by weight) is produced after centrifugation at a temperature that is either 50° C. or in the range of from 45-55° C., at a g-force of either 2000 g or in the range of from 1800-2200 g, over a time period that is 30 minutes or in the range of from 27-33 minutes.

BRIEF DESCRIPTION OF THE DRAWINGS

The present invention will now be described with reference to the accompanying drawings, in which.

DESCRIPTION OF EMBODIMENTS

Parameter Measurement

Figure 1:
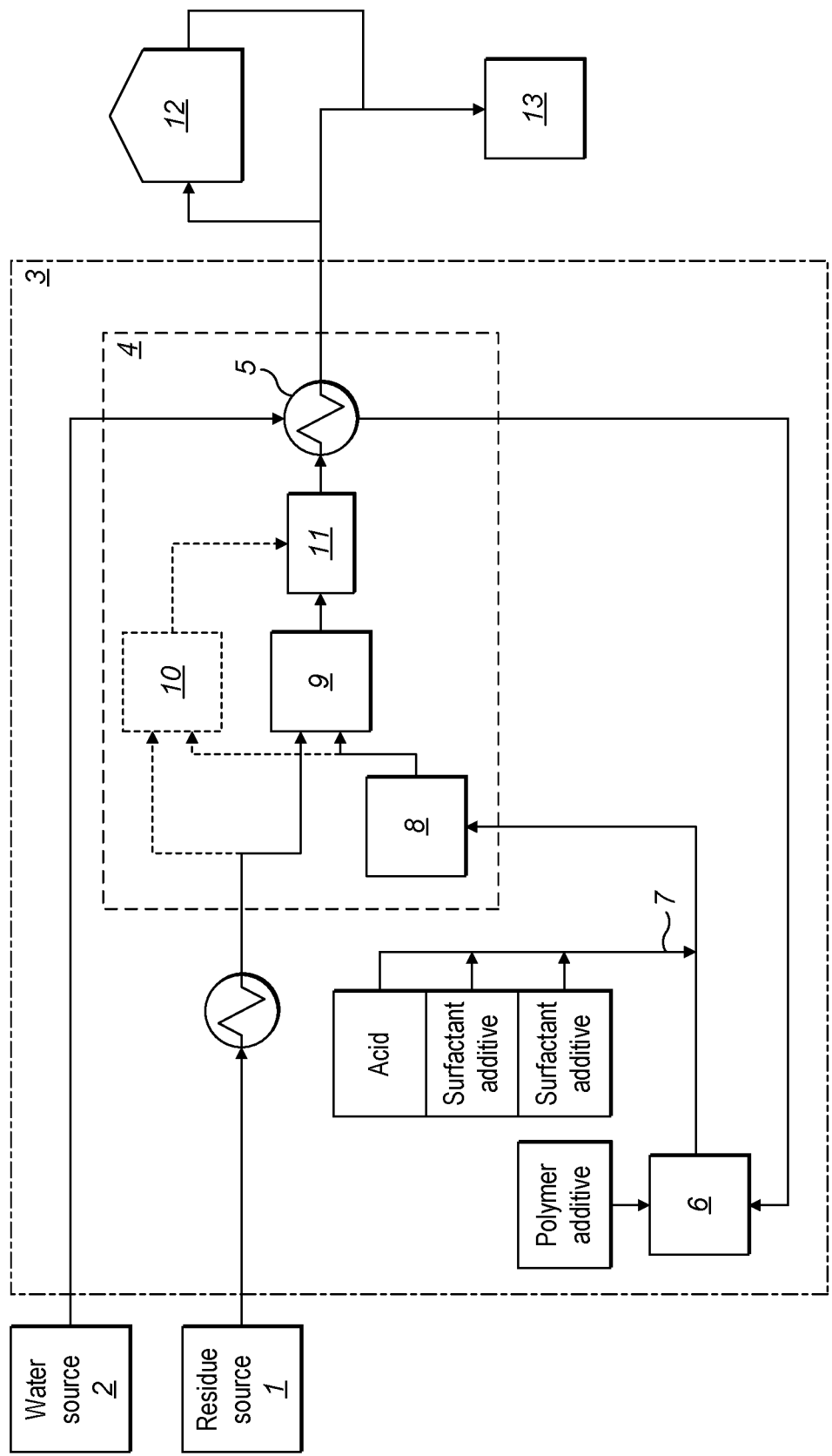
FIG. 1 shows a schematic of a process for producing an oil-in-water emulsion according to the invention.

The average droplet size distribution of the oil phase can be measured by conventional techniques, for example using light scattering techniques using commercially and readily available apparatus, such as a Malvern Mastersizer™ instrument. The average droplet size is expressed as the Volume Moment Mean, represented as the D[4,3] mean. In the present invention, the average droplet size is in the range of from 3 to 15 μm, although is preferably in the range of 5 to 10 μm.

Similar light scattering techniques and apparatus can be used to determine the droplet size distribution, and hence the weight %, of droplets with a size of greater than 125 μm based on the volume equivalent sphere diameter. In the invention, the percent of particles having a size of greater than 125 μm is less than 3 wt %. Preferably it is less than 2 wt %, and more preferably less than 1 wt %. In embodiments, less than 0.5 wt % can be achieved.

The viscosity can also be routinely measured using standard techniques, and equipment such as the Malvern Kinexus™, which measures viscosity at controlled temperature and shear rates. The value is expressed in terms of mPas (cP), and is preferably determined at a shear rate of 20 $s^{-1}$ and at 50° C., although in one embodiment, the shear rate and temperature can differ by up to±10%. In the present invention, the value is in the range of from greater than 100 and up to 700 mPas under such conditions, more preferably in the range of from 200 to 700 mPas.

Static stability refers to the stability of the emulsion during storage. This can conveniently be measured by the centrifugation method according to the third aspect of the present invention, by determining the amount of material (wt %) that deposits from the oil-in-water emulsion.

In the present invention, generally, the method for determining the static stability of an oil-in-water emulsion comprises the steps of:
- providing an oil-in-water emulsion;
- centrifuging the oil-in-water emulsion under predetermined conditions for a pre-determined period of time; and
- determining the amount of residue deposited from the oil-in-water emulsion after the pre-determined period of time to determine the oil-in-water emulsion's static stability.

The centrifuging is typically operated in excess of 1000 g (i.e. g-force), and preferably in the range of from 1000 to 3000 g, for example 1500 to 2500 g. Typically, 2000 g±10% is employed (i.e. 2000 g or in the range of from 1800 to 2200 g).

The temperature is typically in the range of from 40 to 90° C., for example 40 to 60° C., such as 50° C.±10% (i.e. 50° C., or in the range of from 45 to 55° C.).

A typical sample size is in the range of from 1 to 100 mL, for example 5 to 15 mL, e.g. 10 mL±10% (i.e. 10 mL or in the range of from 9 to 11 mL).

A suitable time for centrifugation is from 1 to 60 minutes, for example from 20 to 40 minutes, typically 30 minutes±10% (i.e. 30 minutes or in the range of from 27 to 33 minutes).

Typical conditions include centrifugation at 2000 g for 30 minutes at 50° C., using a sample size of 10 mL.

The static stability is preferably less than 3 wt % residue remaining after centrifugation.

In the oil-in-water emulsion of the present invention, the static stability at 50° C. is such that the residue after centrifugation of a 10 mL sample is less than 5 wt %. Preferably, this quantity is less than 4 wt %, and more preferably less than 3 wt %. In embodiments, a static stability of less than 2.5 wt % can be achieved.

An alternative static stability test is described in U.S. Pat. No. 6,194,472, for example, which involves pouring the emulsion into a 500 mL graduated cylinder, and leaving to stand for 24 hours, after which the hydrocarbon content in each of the top 50 mL and bottom 50 mL is measured, and the difference calculated. This test is qualitative, and does not necessarily provide comparable numerical values. It also takes a long time to complete. The static stability test by centrifugation according to the present invention is advantageous, in that it is rapid, quantitative, and reduces the possibility of degradation or long-term surface wall interactions influencing the results.

Another static stability test is a sieve test for particles greater than 125 μm (120 Mesh), based for example on ASTM tests D4513-85 and D4572-89. An example test (described below) involves passing 100 g of oil-in-water emulsion through a 125 μm sieve, washed with a 2% solution of non-ionic surfactant, such as a nonyl phenol or alkyl ethoxylate, and dried in an oven for 2 hours prior to weighing. Typically, in the compositions according to the present invention, the amount of material captured and remaining on the sieve is preferably less than 3 wt %, more preferably less than 1 wt %, more preferably 0.5 wt % or less. Although this test can provide some information on the extent of larger particles in the emulsion, a "before and after" analysis still has to be conducted over several hours (e.g. 24 hours). In addition, it only provides information on the presence or formation of larger particles, even though smaller droplets may be non-emulsified, and which may settle over longer periods of time. The present static stability centrifugation test overcomes such disadvantages.

Dynamic stability is a measure of the stability of the emulsion when under motion or agitation. It can be measured using a pump test.

An example of a pump test is described below, and involves pumping emulsion from a storage tank and through a recirculation loop over a 30 minute period, and measuring the change in droplet size distribution. In the example described in further detail below, 10 kg emulsion is passed via a screw-pump from a storage tank and through a recirculation loop for 30 minutes. The recirculation loop has a volume of 2.4 L, based on a length of 4.7 m and a piping internal diameter of 25 mm. The pump rate is 370 kg/h.

In the oil-in-water emulsion of the present invention, the dynamic stability is expressed in terms of change in droplet size distribution in the above pump test. In the particular, the change in D[4,3] average particle size at 50° C. over the 30 minute period must be less than 0.3 μm. In embodiments, the 50° C. temperature can vary by up to±10%. In embodiments, the 30 minute period can vary by up to±10%.

Another pump test is described in U.S. Pat. No. 6,194,472. This involves first filtering 2 kg of oil-in-water emulsion through a 50-mesh filter, then pumping (using a progressive cavity pump) the filtered emulsion through a 50 mesh filter for 18 minutes and determining the amount of material collected by the filter.

An alternative test is a Shaker Table test, which employs 100 mg sample, and subjects it to 24 hours of agitation at 3.3 Hz/200 rpm at 40° C. at a stroke setting of 18 mm. Stability is determined by the amount (weight) of material deposited when filtered through a 120 mesh (125 μm) sieve. This test is described in more detail below.

U.S. Pat. No. 6,194,472 describes another shaker test, in which 100 g sample is shaken in a Burnell Wrist Action™ Shaker for 24 hours, and then determining the amount of residue remaining on a 50 mesh screen.

Mesh sizes referred to herein are based on US mesh sizes.

The dynamic stability test according to the present invention offers a number of advantages over the prior art methods. In particular, by measuring particle/droplet size distribution rather than merely the proportion of droplets/particles above a particular mesh size, the rate of change of droplet size can be measured, which provides a more robust indication of the emulsion properties can be established, leading to an improved ability to predict the long-term handling stability of the emulsion. In addition, from a practical point of view, avoiding the need to filter and weigh the residue is simpler and requires less manual operating steps, particularly where on-line droplet size measurements can be made.

Oil Phase

The oil phase of the invention comprises hydrocarbons. Typically the oil is a source of heavy hydrocarbons, which may have a density slightly lower to significantly higher than water (e.g. 0.95 to 1.15 kg/m$^3$ or 0.95 to 1.25 kg/m$^3$ at 15° C.). The heavy hydrocarbon may have an extremely high viscosity. For example, the viscosity can be up to 300 000 cSt at 100° C. It can employ residues or hydrocarbon sources which have viscosities of 7 cSt or more at 25° C., or 10 cSt or more at 100° C. The invention can also utilise hydrocarbon sources having viscosities of 180 cSt or more at 25° C., and preferably 250 cSt or more at 25° C. The oil-phase hydrocarbons can be sourced from a number of established processes, including:
- processed natural heavy crude oil or natural bitumen (typically after de-sanding, de-salting, de-watering)
- refinery atmospheric distillation
- refinery vacuum distillation
- refinery visbreaking or thermal cracking or steam cracking
- refinery cat-cracking (thermal and catalytic)
- refinery hydroprocessing and hydrocracking
- de-asphalting processes.

In one embodiment the oil-in-water emulsion comprises an oil phase which is a hydrocarbon residue, e.g. being sourced from refinery residues with kinematic viscosities of up to 300 000 cSt at 100° C., and preferably above 200 cSt at 100° C., and more preferably above 1 000 cSt at 100° C. Examples of hydrocarbon residues that can be used in the oil-in-water emulsion of the present invention are given in Table 1.

TABLE 1

Examples of hydrocarbon residues

| Residue Type | CAS RN | Description |
| --- | --- | --- |
| Asphalt | 8052-42-4 | Combination of high molecular weight oil derived compounds with high proportion of carbon numbers >C25. |
| Residue (petroleum), atm. Tower | 64741-45-3 | A residue produced from the atmospheric distillation of crude oil. Combination of high molecular weight oil derived compounds with high proportion of carbon numbers >C20, and boiling at >350° C. (662° F.). |
| Residue (petroleum), vacuum | 64741-56-6 | A residue produced from the vacuum distillation of residue coming from the atmospheric distillation of crude oil. Combination of high molecular weight oil derived compounds with high proportion of carbon numbers >C34, and boiling at >495° C. (923° F.). |
| Residue (petroleum), catalytic reformer fractionator | 64741-67-9 | A residue produced from the distillation of product derived from a catalytic reformer process. Combination of high molecular weight oil derived compounds with high proportion of carbon numbers C10-C25, and boiling range 160-400° C. (320-725° F.). |
| Residue (petroleum), hydrocracker | 64741-75-9 | A residue produced from the distillation of product derived from a hydrocracking process. Combination of high molecular weight oil derived compounds with high proportion of carbon numbers >C20, and boiling >350° C. (662° F.). |
| Residue (petroleum), thermal cracked | 64741-80-6 | A residue produced from the distillation of product derived from a thermal cracking process. Combination of high molecular weight oil derived compounds with high proportion of carbon numbers >C20, and boiling >350° C. (662° F.). |
| Raffinates (petroleum), residual oil decarbonation | 64742-07-0 | Combination of hydrocarbons obtained as the solvent insoluble fraction from C5-C7 solvent decarbonisation of a residue with high proportion of carbon numbers >C34, and boiling >495° C. (923° F.). |
| Residue (petroleum), hydrodesulphurised atmospheric | 64742-78-5 | A residue produced from treating an atmospheric tower residue with hydrogen (in the presence of a catalyst), primarily to remove sulphur. Combination of high molecular weight oil derived compounds with high proportion of carbon numbers >C20, and boiling >350° C. (662° F.). |
| Residue (petroleum), hydrodesulphurised atmospheric | 64742-85-4 | A residue produced from treating an vacuum tower residue with hydrogen (in the presence of a catalyst), primarily to remove sulphur. Combination of high molecular weight oil derived compounds with high proportion of carbon numbers >C34, and boiling >495° C. (923° F.). |
| Residue (petroleum), catalytic reformer fractionator residual distillation | 68748-13-7 | A residue produced from the distillation of catalytic reformer process residue. Combination of high molecular weight oil derived compounds with that boil >399° C. (750° F.). |
| Residue (petroleum), coker scrubber condensed ring aromatic containing | 68783-13-1 | Combination of hydrocarbons obtained as the residual fraction from the distillation of vacuum residue and the products from a thermal cracking process, with high proportion of carbon numbers >C20, and boiling <350° C. (662° F.). |
| Residue (petroleum), solvent extracted vacuum distilled atmospheric residue | 70913-85-8 | A residue produced by the solvent extraction of a vacuum distillate of a residue from the atmospheric distillation of crude oil |
| Asphaltenes (petroleum), | 91995-23-2 | Combination of hydrocarbons obtained as a complex solid black product by the separation of petroleum residue by means of a special treatment of a light hydrocarbon cut. The carbon/hydrogen ratio is especially high. |

TABLE 1-continued

Examples of hydrocarbon residues

| Residue Type | CAS RN | Description |
| --- | --- | --- |
| Residue (petroleum), thermally cracked vacuum | 92062-05-0 | Combination of hydrocarbons obtained from the vacuum distillation of the products from a thermal cracking process, with high proportion of carbon numbers >C34, and boiling >495° C. (923° F.). |

An example hydrocarbon residue that can be used is given in Table 2.

TABLE 2

Example of hydrocarbon residue

| Property | Typical VDU, visbreaker or vacuum flashed visbreaker residue. |
| --- | --- |
| Viscosity, cSt | max. 150,000 at 100° C. |
| Density g/ml | max. 1.08 at 15° C. |
| Sulphur, % wt. | max. 3.5 |
| Al/Si content, ppm | max. 10 |
| P-value (if applicable) | min. 1.05 |
| Filterable solids | None |

Oil-in-water emulsions according to the invention can typically contain 60% wt or more of the "oil" phase, e.g. the hydrocarbon residue. In embodiments, the emulsion comprises in the range of from 60 to 80 wt % of the oil phase.

Aqueous Phase

The water in the aqueous phase can come from a variety of sources. An example of a water specification that can be used is given in Table 3.

TABLE 3

Example of water specification for oil-in-water emulsion production

| Parameter | Value |
| --- | --- |
| Suspended solids | Less than 10 mg/l and Filtered to 35 μm |
| Chlorides, mg/l | Less than 50 |
| Alkali metals, mg/l | Less than 20 |
| Alkaline earth metals, mg/l | Less than 30 |
| Silicon as SiO$_2$, mg/l | Less than 40 |
| pH | 6.5 to 8 |
| Total hardness | Max 6°dH |

Optionally, the water can be pretreated, for example by filtration and/or deionization. The water can come from a variety of sources, and from number of processes, including;
    filtered fresh water,
    potable water, and
    refinery or heavy oil upgrading waste or sour stripping water.

The water content of the oil-in-water emulsions of the present invention is typically in the range of from 20 to 40 wt %.

Chemical Additives

The oil-in-water emulsion comprises one or more chemical additives. These can include one or more of the following:
    Primary surfactant
    Secondary surfactant
    Polymeric stabiliser
    Acid The chemical additives are typically added to the aqueous phase before mixing with the oil phase when preparing the oil-in-water emulsion of the present invention.

The chemical additives can be provided separately, or two or more additives can be provided in the form of a pre-prepared chemical additive package.

Advantageously, the chemistry of the additives is taken into consideration to ensure they do not contribute to any detrimental performance during use, for example as a fuel, such as avoiding negative impact on health and the environment, disadvantageous corrosion both before and post-combustion, and any increased burden of undesirable combustion emissions.

Primary Surfactants

The oil-in-water emulsion of the invention comprises at least one primary surfactant, which is typically added to the aqueous phase before being mixed with the oil phase when preparing the oil-in-water emulsion.

The primary surfactant is typically present in an amount ranging from 0.05 to 0.6% wt of the oil-in-water emulsion. The aim of the primary surfactant is to act as an emulsifier, to stabilise the oil phase droplets in the aqueous phase. A range of from 0.05 to 0.5 wt % primary surfactant can be used, for example 0.08 to 0.4 wt %.

A number of primary surfactants can be employed. They can include non-ionic, anionic, amphoteric, zwitterionic and cationic surfactants. There can be one primary surfactant or more than one primary surfactant. In embodiments, at least one primary surfactant, optionally all the primary surfactants, is selected from one or more of the following:
    fatty alkyl amines according to the formula;

$$R^a\text{—[NH(CH}_2)_m]_p\text{—NH}_2$$

where;
$R^a$ is an aliphatic group having 12 to 24 carbon atoms
m is a number 2 or 3
p is a number 0 to 3
    ethoxylated fatty alkyl amines according to the formula;

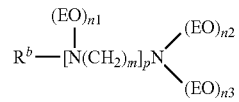

where;
$R^b$ is an aliphatic group having from 12 to 24 carbon atoms
m is a number 2 or 3
p is a number 1 to 3
n1, n2 and n3 are each independently a number within the range greater than 0 to 70, for example from 2 to 70, or from 3 to 70. In one embodiment, n1+n2+n3 is a number greater than 0 and up to 210. Each of n1, n2 and n3 may or may not be an integer.

ethoxylated fatty alkyl monoamines according to the formula;

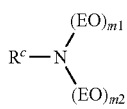

where;
R$^c$ is an aliphatic group having from 12 to 24 carbon atoms
m1 and m2 are each a number within the range greater than 0 and up to 70, for example from 2 to 70, or from 3 to 70. In one embodiment, m1+m2 is a number greater than 0 and up to 140. Each of m1 and m2 may or may not be an integer.
methylated fatty alkyl monoamines according to the formula;

where;
one or two of the groups R$^1$, R$^2$, and R$^3$ are each independently selected from aliphatic groups having from 8 to 22 carbon atoms
the remaining groups of R$^1$, R$^2$, and R$^3$ are methyl;
methylated fatty alkyl amines according to the formula;

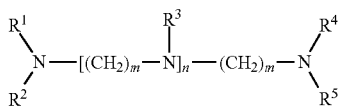

where;
one or two of the groups R$^1$ to R$^5$ are independently selected from aliphatic groups having from 8 to 22 carbon atoms
the remaining groups of R$^1$ to R$^5$ are methyl
n is an integer from 1 to 5
m is 2 or 3,
or according to the formula;

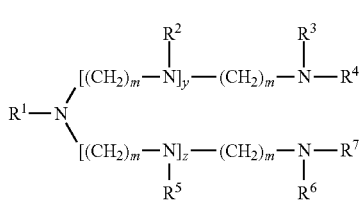

where;
one or two of the groups R$^1$ to R$^7$ are each selected from aliphatic groups having from 8 to 22 carbon atoms
the remaining groups of R$^1$ to R$^7$ are methyl
m is 2 or 3
y and z are integers from 0 to 4, and (y+z) is 0 to 4;

or according to the formula;

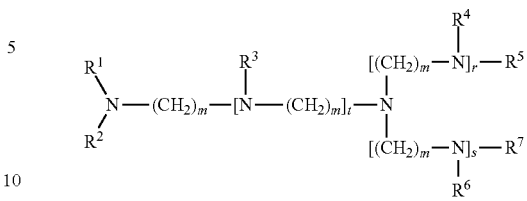

where;
one or two of the groups R$^1$ to R$^7$ are an aliphatic group containing 8 to 22 carbon atoms the remaining groups of R$^1$ to R$^7$ are methyl
m is 2 or 3
t is between 0 to 3
r and s are between 1 to 4, and (t+r+s) is between 2 to 5;
and;
quaternary fatty alkyl amines according to the formula;

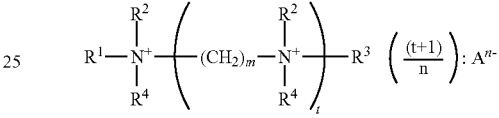

where;
R$_1$ is an aliphatic group having 12 to 24 carbon atoms, e.g. —(CH$_2$)$_y$—CH$_3$, optionally comprising a carbonyl group adjacent to the nitrogen atom, i.e. —C(O)—(CH$_2$)$_{(y-1)}$—CH$_3$, where y is from 10 to 22;
R$^2$ and R$^3$ are independently at each occurrence selected from H or an aliphatic group having from 1 to 6 carbon atoms, preferably from 1 to 3 carbon atoms, and more preferably 1 carbon atom;
R$^4$ is selected from H or a C$_{1-4}$ aliphatic group;
m is 2 or 3;
t is from 0 to 4
A is an anion;
n is the valence of the anion.

The aliphatic groups mentioned in the formulae above, including those containing a carbonyl group, can optionally be substituted, typically with one or more, for example from 1 to 3, substituents which are independently selected from hydroxyl, C$_{1-3}$ alkyl, C$_{1-3}$ alkoxy, or C$_{1-3}$ hydroxyalkyl. Preferably, there are no substituents on the aliphatic groups. Each aliphatic group can be saturated, or can comprise double or triple carbon-carbon bonds, for example up to 6 double bonds, for example up to 3 double bonds.

Preferably, R$^1$ has a formula C$_{14-20}$H$_{24-41}$, or C(O)C$_{13-19}$H$_{22-39}$. More preferably it has a formula C$_{14-20}$H$_{24-41}$.
Preferably, each R$^2$ and R$^3$ is independently selected from CH$_3$, H and CH$_2$CH$_2$OH.
Preferably, each R$^4$ is independently selected from CH$_3$ and H.
Examples of fatty alkyl amines include:
quaternary fatty alkyl monoamines according to the formula;

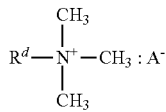

where;
R$^d$ is an aliphatic group having 12 to 24 carbon atoms
A is an anion;
and
quaternary fatty alkyl diamines according to the formula;

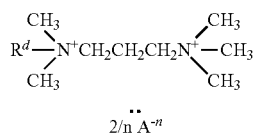

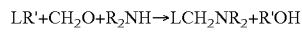

where;
R$^d$ is an aliphatic group having 12 to 24 carbon atoms
A is an anion
n is the valence of the anion;

In the above, the anion A is preferably selected from those anions which bind more strongly to the quaternary amine than carbonate. Examples include halide, particularly Cl$^-$, and organic anions such as formate (HCOO$^-$), acetate (CH$_3$COO$^-$) and methane sulfonate (CH$_3$SO$_3^-$).

In the above, the group "EO" is an ethoxylate group (—CH$_2$CH$_2$O—). The ethoxylate group (or polyether group for more than one linked ethoxylate group) is typically terminated by H, i.e. —CH$_2$CH$_2$OH.

In embodiments, the primary surfactant is selected from one or more fatty alkyl di-, tri- and tetra-amines, ethoxylated fatty alkyl mono-, di- and tri-amines, and quaternary fatty alkyl amines.

In further embodiments, the primary surfactant is selected from one or more fatty alkyl diamines, fatty alkyl tetra-amines, ethoxylated fatty alkyl diamines, and quaternary fatty alkyl amines. Examples include fatty alkyl tripropyl-enetetramine, such as tallow tripropylenetetramine, fatty alkyl propylene diamines, oleyldiamine ethoxylate.

The term "fatty alkyl" includes not only saturated groups (i.e. C$_{12}$ to C$_{24}$ alkyl groups), but also partially unsaturated C$_{12}$ to C$_{24}$ groups (i.e. C$_{12}$ to C$_{24}$ alkenyl groups), for example having up to six C=C double bonds. Preferred fatty alkyl groups have no more than 3 double bonds. Examples of fatty alkyl groups include oleyl (C18, 1 double bond), and other groups associated with tallow, e.g. palmityl (C16, 0 double bonds), stearyl (C18, no double bonds), myristyl (C14, no double bonds), palmitoleyl (C16, 1 double bond), linoleyl (C18, 2 double bonds) and linolenyl (C18, 3 double bonds).

Secondary Surfactant

The oil-in-water emulsion typically, and preferably, comprises a secondary surfactant. Typical amounts present in the oil-in-water emulsion are in the range of from 0 to 2 wt %, and preferably greater than 0.3 wt %, for example at least 0.4 wt %.

Secondary surfactants serve to improve dynamic stability of the resulting oil-in water emulsion, to ensure they remain stable during handling and use. This is advantageous for fuel applications, and particularly for marine fuel applications where the fuel handling conditions are relatively severe in terms of pumping, shearing and large changes in pressure, and also where the fuel is subject to significant motion over extended periods of time.

They can include non-ionic, anionic, amphoteric, zwitterionic and cationic surfactants.

Typically secondary surfactants have larger hydrophilic groups compared to the primary surfactants, and thereby impart a degree of steric stabilisation into the emulsion system. There can be one or more than one secondary surfactant. At least one of the secondary surfactants, optionally all, is preferably selected from one or more lignin amines.

Particularly preferred lignin amines are made by a Mannich reaction, for example between lignin, formaldehyde and a secondary amine, according to the formula;

LR'+CH$_2$O+R$_2$NH→LCH$_2$NR$_2$+R'OH

In the above formula, L represents lignin, and R' is a displaceable hydrogen or a cation such as an alkali metal (e.g. sodium) on the lignin. Each R on the amine can be independently selected from an optionally substituted aliphatic group having from 1 to 6 carbon atoms. Dimethylamine is an example of a secondary amine which can be used. Although formaldehyde is typically used, aldehydes other than formaldehyde can be employed, for example aldehydes with an aliphatic group having from 1 to 6 carbon atoms.

Optional substituents on the aliphatic group are the same as those identified above for the various exemplary primary surfactants.

The lignin can be used in a salt form, for example in a form where displaceable hydrogens are at least in part replaced with an alkali metal ion, such as sodium.

Production of lignin amines is described for example in U.S. Pat. Nos. 2,709,696, 2,863,780 and 4,781,840.

Polymeric Stabiliser

One or more polymeric stabiliser can optionally be added to the aqueous phase when preparing the oil-in-water emulsion of the present invention. When present, they are preferably included in amounts of up to 0.25 wt % of the oil-in-water emulsion. In embodiments, they are present in amounts in the range of from 0.03 to 0.08 wt %.

Polymeric stabilising and flow improvement agents are used to improve static stability in storage by compensating for the density differential between the residue and aqueous phase. They can also modify the viscosity characteristics of the emulsion.

The polymer stabilising additive can form a weakly 'gelled' structure in the aqueous additive-containing phase, which helps to improve static stability of the oil-in-water emulsion by holding the hydrocarbon residue droplets apart, preventing sedimentation during static storage conditions. The weak gel structure can also impart low resistance or yield to applied stress to ensure suitable low viscosity characteristics of the emulsion, for example during pumping and handling. This behaviour can also be recoverable, for example once the oil-in-water emulsion fuel is pumped into a tank it can recover its static stability characteristics. The polymer additive can help to achieve this by interacting with the other additives in the formulation through entanglement and bonding mechanisms, forming a molecularly structured gel.

There can be one or more than one polymeric stabiliser and flow improving agent. At least one, optionally all, are preferably selected from one or more alkyl hydroxyalkyl cellulose ethers (water soluble), preferably having an alkyl group with 1 to 3 carbon atoms, and an hydroxyalkyl group (e.g., hydroxyethyl or hydroxypropyl), where;
DS$_{alkyl}$ is in the range of from 0.1 to 2.5;
MS$_{hydroxyalkyl}$ is in the range of from 0.2 to 4.0;
weight average molecular weight is in the range of from 100,000 to 2,000,000 Da (ideally from 800,000 to 1,600,000 Da);

Examples include methyl ethyl hydroxyethyl cellulose ether (water soluble), preferably having $DS_{methyl}$ in the range of from 0.3 to 1.5
$DS_{ethyl}$ in the range of from 0.1 to 0.7
$MS_{hydroxyethyl}$ in the range of from 0.2 to 3.0.

DS represents the degree of substitution of the specified component, and MS represents the extent of molar substitution of the specified component.

Further examples include those where (in the formula represented below) R is H, $CH_3$ and/or $[CH_2CH_2O]_nH$.

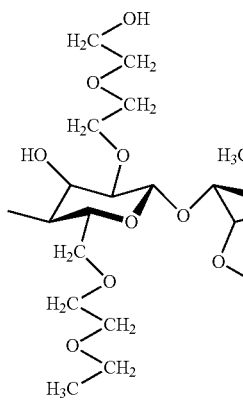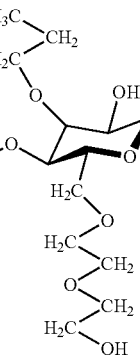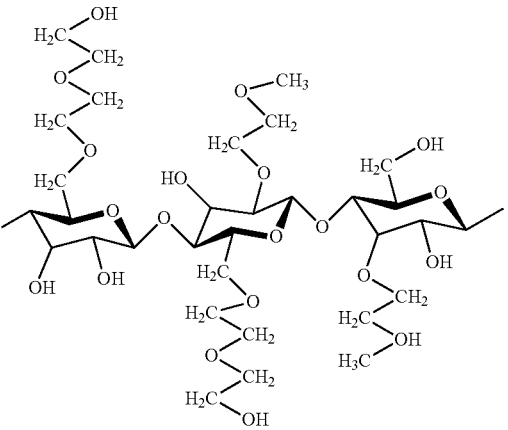

Other examples of polymeric stabiliser and flow improvement agent can include guar gum, starch and starch derivatives, hydroxy ethyl cellulose, and ethyl hydroxy ethyl cellulose.

Acid

An acid, i.e. a Brnsted acid, is often used to activate the primary surfactant. The aqueous phase preferably has a pH in the range of pH 2 to 6, and more preferably in the range 2 to 4.5 or 3 to 4.5. This also generally corresponds to the pH of the resulting oil-in-water emulsion.

Acids can be organic or inorganic. Inorganic acids include hydrochloric acid (HCl), sulfuric acid ($H_2SO_4$) and nitric acid ($HNO_3$). Organic acids comprise at least one C—H bond, examples of which include methanesulfonic acid, formic acid, acetic acid, citric acid, and benzoic acid. There can be one or more than one acid.

The acid should preferably not be detrimental to the operational or environmental performance of the oil-in-water emulsion fuel, nor be incompatible with any other components of the oil-in-water emulsion, for example the other chemical additives used. In marine fuel applications, for example, inorganic acids are often prohibited, hence organic acids are preferred.

Where organic acids are used, at least one of which (optionally all) is preferably selected from methanesulfonic acid, formic acid, acetic acid, citric acid, and benzoic acid. Preferably at least one (optionally all) of the acids are selected from formic acid and methanesulfonic acid.

Acids that yield a divalent anion (such as sulfuric acid) can act to block the interfacial action of ionic primary and secondary surfactants, hence acids that yield a monovalent anion are preferred.

Oil-in-Water Emulsions as Fuels

In embodiments, an oil-in-water emulsion fuel according to the invention comprises one, more than one, or all of the characteristics defined in Table 4.

TABLE 4

An embodiment of an oil-in-water emulsion suitable for use as a fuel

| Component | Typical Range (% wt) |
|---|---|
| Hydrocarbon Residue | 60 to 80 |
| Water | 20 to 40 |
| Primary surfactant | 0.05 to 0.2 |
| Secondary surfactant | 0 to 2 |
| Polymeric stabiliser | 0 to 0.25 |
| Acid | to achieve a pH in the range 2 to 4.5 |

Oil-in-water emulsion fuels according to the invention have properties that enable them to be utilised within existing combustion engines or boilers, for example by being:

- sufficiently stable and robust to withstand storage in static tanks and when subjected to motion, for example the motion of sea-going vessels, for prolonged periods (from months to over a year);
- able to be handled by existing fuel systems (e.g. pumping and heating systems) for conventional oil based fuels;
- fungible with other oil-in-water emulsion fuels or conventional oil based fuels (e.g. to permit fuel switching in Emission Control Areas or during system start-up/shut down)
- able to be used within the allowable and feasible scope of a vessel engine's permitted range of operational settings without significant modifications or amendment to technical codes.

The oil-in-water emulsion of the invention can be used as a fuel, or as a component of a fuel composition. It can be used in heating oil applications, for example in boilers, which may otherwise use fuels such as kerosene or gas oil. It can also be used in engines, typically diesel engines that use fuels such as diesel fuel or bunker fuel. The oil-in-water emulsion fuels of the invention are particularly suited for marine vessel applications, where high static and dynamic stabilities are required.

Preparation of an Oil-in-Water Emulsion

The oil-in-water emulsion can be prepared by a process in which water and the one or more chemical additives are mixed to form the aqueous phase; heating a hydrocarbon-containing oil; and blending the hydrocarbon-containing oil and the aqueous phase to form an oil-in-water emulsion.

It is preferred that the chemical additives form an aqueous solution when mixed with water, although a suspension or emulsion can be tolerated provided there is sufficient mixing with the hydrocarbon oil-containing phase to ensure a stable oil-in-water emulsion results.

Examples of the hydrocarbon-containing oil are provided above. It is preferably heated to a temperature sufficient to reduce its viscosity to below 500 cSt, for example in the range of from 100 to 500 cSt or 200 to 500 cSt.

Preferably, it is heated to a temperature such that, when mixing with the aqueous phase, the resulting temperature at the oil-water interface will be such that the viscosity of the oil phase is less than 10000 cSt. This will depend on the heat capacities of the aqueous phase (which incorporates the chemical additives) and the hydrocarbon-containing oil, and also their relative concentrations.

The relationship between the temperature at the interface and the initial temperatures of the aqueous and oil phases can be expressed by the following equation:

$$T_{aq} = T_i + \left\{ (T_i - T_{oil}) \times \left( \frac{C_{oil}}{C_{aq}} \right) \times \left( \frac{[oil]}{[aq]} \right) \right\}$$

In the above equation:
$T_i$=temperature at the oil/water interface of the oil-in-water emulsion
$T_{oil}$=temperature of oil phase before mixing (° C.)
$T_{aq}$=temperature of aqueous phase before mixing (° C.)
$C_{oil}$=specific heat capacity of oil phase (kJ/kg/° C.)
$C_{aq}$=specific heat capacity of aqueous phase (kJ/kg/° C.)
[oil]=proportion of oil phase (wt %)
[aq]=proportion of aqueous phase (wt %)

The temperature of the oil phase ($T_{oil}$) before mixing is preferably such that the hydrocarbon-containing oil viscosity is in the range of from 200-500 cSt. Although this is dependent on the source of hydrocarbons, it is typically in a range of from 110 to 230° C.

The temperature at the oil/water interface after mixing ($T_i$) is preferably such that the viscosity of the hydrocarbon-containing oil is less than 10 000 cSt. This temperature is preferably less than the boiling point of the aqueous phase, and also a temperature at which the thermal and phase stability of the chemical additives is preserved. Typically, this temperature is in the range of from 70 to 150° C., for example from 80 to 120° C.

The temperature of the aqueous phase before mixing ($T_{aq}$) is selected according to the above requirements of the $T_i$ and $T_{oil}$ temperatures. Typically, it is in the range of from 30 to 95° C., for example from 50 to 90° C., or 50 to 70° C.

The relative weight ratio of the hydrocarbon-containing oil relative to the aqueous phase are typically in a range of from 5:1 to 1:1, and preferably in a range of from 4:1 to 3:2 or from 4:1 to 2:1.

Mixing to form the emulsion can be achieved using apparatus and technology known to a skilled person, such as high shear mixing apparatus.

In one embodiment of the invention, two separate and different emulsions are separately prepared and mixed to form a composite oil-in-water emulsion, which enables further control over the properties of the desired oil-in-water emulsion to be achieved.

A non-limiting example schematic of a process for preparing an oil-in-water emulsion according to the invention is given in FIG. 1. The area designated (1) represents the source of hydrocarbon-containing oil to be utilised as the oil phase for the production of the oil-in-water emulsion.

The area designated (2) represents the source of suitable water.

In the area designated (3), the material from the hydrocarbon-containing oil source (1) may be cooled by a medium to a suitable temperature for storage as required and further temperature control as required, to achieve a viscosity of between 250 to 500 cSt, for direct introduction into the emulsion preparation unit (4). Water (2) is first heated (typically to within the range 50 to 90° C.) in a heat exchanger (5) that is also utilised for cooling the final emulsion product (typically to less than 90° C.) along with supplementary cooling (typically to less than 60° C.) to enable easier handling.

In area (6), a polymer stabiliser can be mixed into the aqueous phase if and as required, followed by the further addition (7) of additional chemical additives (including one or more of the primary surfactant and secondary surfactant), and optionally also a suitable acid if pH adjustment is required. The chemical additives can be varied if and as required to achieve an emulsion fuel with the required specification and performance criteria.

The chemical additives used preferably do not contain any components or impurities that can negatively affect the use of the resulting emulsion as a fuel. Therefore, preferably, they contribute no more than 50 ppm of halogenated compounds and no more than 100 ppm of alkali metals in the final emulsion fuel specification.

The aqueous phase containing the chemical additives passes through a tank/vessel (8), which provides sufficient residence time for any added acid to fully activate other chemical additives, for example the primary surfactant. Both the aqueous phase and the hydrocarbon-containing oil phase are then introduced into a high-shear colloidal mill (9), the speed of which is adjusted to intimately mix the components. One or more colloidal mills may be employed (10) within the manufacturing process, depending on the number of required emulsion component streams of differing properties (i.e., one for the manufacture of a single component emulsion fuel, or two or more required for the manufacture of a composite, multi-component emulsion fuel). If more than one component is manufactured, then the differing components can be passed through an in-line blender (11) or mixed downstream at the required ratios to achieve the correct properties of the final oil-in-water emulsion fuel. In this way, the characteristics of the final required droplet size distribution, hydrocarbon/water phase ratio (i.e. energy density) and viscosity/rheological characteristics can be effectively controlled.

After production, the emulsion fuel may be stored (12) for subsequent transport and supply for use as a fuel (13).

Process of Hydrocarbon Residue Evaluation, Formulation and Emulsification

The formulation of the oil-in-water emulsion can be optimised, depending on the nature of the hydrocarbon-containing oil, typically a hydrocarbon residue such as one of those listed in Table 1.

The chemical additives and their concentrations that can be used for different hydrocarbon residues can be optimised by a skilled person, and preferably the components are chosen so as to ensure compliance with any associated operational, performance or legislative requirements.

Taking an example of an oil-in-water emulsion fuel, the formulation can be optimised by hydrocarbon analytical testing, followed by a series of laboratory and pilot scale emulsification and emulsion handling tests. The objectives of these tests are to:

- characterise the properties of the hydrocarbon source that is to be used as the oil-phase (i.e. physical and chemical properties),
- characterise the hydrocarbon emulsification process (e.g. by selection and adjustment of primary surfactants, aqueous-phase and hydrocarbon compositions and temperatures, pH, mixer speed, single pass or composite manufacture, etc.),
- optimise the resulting emulsion fuel static stability (e.g. by including the use of polymeric stabiliser additives) both in the short term (immediately after production) and in the medium/long term (weeks/months), and
- optimise the resulting emulsion fuel dynamic stability (e.g. by varying the aqueous phase composition, typically by the additional inclusion of a secondary stabilising surfactant).

The target specification of the resulting oil-in-water emulsion fuel at each stage is based on correlation with established (acceptable) performance criteria of emulsion fuels during full application (i.e., behaviour during storage, supply and logistics handling, as well as during end-use engine operation). A typical example of an oil-in-water emulsion fuel specification is given in Table 5.

In further embodiments, the oil-in-water emulsion of the invention can have the following characteristics, which is suitable for use as a marine fuel:

Median (50% v) Droplet Size (D(v,0.5)): 15 µm Max;

90% v Droplet Size (D(v,0.9)): 75 µm Max;

Viscosity, (50° C., 100 $s^{-1}$); 180 mPas Max;

Sieve Test (at 150 µm); 2% wt Max.

Examples of test methods that can be used to measure the above properties are provided in Table 5. The droplet size measurements can be measured using available equipment, such as a Malvern particle size analyser (e.g. using light diffraction methods). The viscosity can be measured using a coaxial cylinder viscometer, and the sieve test can be carried out according to methods such as ASTM D 4513-85, D 4572-89 and ASTMD244/ASTM D6933.

Optionally, the oil-in-water emulsion can also have the properties set out in Table 6.

TABLE 6

Example oil-in-water properties before dynamic stability test

| Parameter | Specification | Suggested Test Method |
|---|---|---|
| Water Content, % wt | 33 Max | IP74/92 (ASTM D95) or IP 358 (ASTM 4006-81) |
| Sulfur, % wt | 2.45 Max | IP 242 |
| Aluminium/Silicon, ppm | 10 Max | IP 501/IP 470 |
| Sodium, mg/kg (ppm) | 100 Max | IP 501/IP 470 |
| Zinc, mg/kg (ppm) | 15 Max | IP 501/IP 470 |
| Phosphorus, mg/kg (ppm) | 15 Max | IP 501/IP 470 |
| Calcium, mg/kg (ppm) | 30 Max | IP 501/IP 470 |

TABLE 5

Parameters of an example target emulsion specification.

| Parameter | Required specification | Method/Equipment |
|---|---|---|
| Optimised characteristics in terms of dispersed residue droplet size distribution to provide enhanced combustion efficiency (>99% carbon conversion) | 3 to 15 µm average (D[4,3] mean) | Laser Light Scattering/e.g., using a "Malvern" Particle Sizer |
| Discrete size distribution of droplets greater than 125 µm (expressed as % weight) to enable fine filtration required for marine engine operation | <3% wt | Laser Light Scattering/e.g., using a "Malvern" Particle Sizer |
| Optimised rheological and hydraulic properties to meet the requirements of functionality and use | >100 to 250 mPas at 20 $s^{-1}$/50° C. | Concentric Cylinder or Cone and Plate Viscometry/e.g., "Malvern" Kinexus Rheometer |
| Maximised energy content, in terms of hydrocarbon concentration (>25 MJ/kg as emulsion fuel) | 67% minimum to typically 80% maximum | Distillation/e.g., ASTM D-95 |
| Static Stability (by centrifugation) | <5% residue | Centrifugation/see test below |
| Static Stability (by sieve test) | <3% residue | Sieve test/e.g., based on the standard ASTM test methods D4513-85 and D4572-89, and ASTMD244/ASTM D6933/ see test below |
| Dynamic Stability (by Shake Table test) | <3% residue | Controlled agitation/see test below |
| Dynamic Stability (by controlled shear) | rheological stability to applied shear between 0.5 to 1000 $s^{-1}$ | Cone and Plate Viscometry/ e.g., "Malvern" Kinexus Rheometer, see test below |
| Dynamic Stability (by pump test) | <0.30 µm increase in mean (D[4,3]) droplet size/min | Pump recirculation/see test below |
| Stability during long-term storage | Ability to retain above properties for >6 months | All of above |

TABLE 6-continued

Example oil-in-water properties before dynamic stability test

| Parameter | Specification | Suggested Test Method |
|---|---|---|
| Hydrogen Sulfide, ppm | 2 Max | IP 570 Part A |
| Flash Point, ° C. | 60 Min | IP 303-93, ASTM D93 or ASTM D3828-81 |

Quality Assurance

Static stability is a term used to describe the stability that an emulsion requires to remain integral under conditions where there is no externally applied force except for gravity (i.e., stability under static storage conditions over time).

Dynamic stability is a term used to describe the stability an emulsion requires to ensure it can be handled as required within the application for which it is designed. This includes being stable when pumped, heated, and used within specific fuel handling components such as pressure control valves, flow meters, fuel injection equipment, etc. This differs from static stability in that it involves the external impartation of energy to the emulsion system (which includes mechanical energy such as shearing and turbulent flow forces) and heat energy (e.g., heating within heat exchangers). As such the oil-in-water emulsion fuel requires a significantly higher degree of dynamic stability than that needed under static conditions.

The physical and chemical properties of a candidate hydrocarbon residue influence the properties of the resulting emulsions, and hence influence the action and efficiency of the chemical additives used.

Therefore the formulation derived for each residue (i.e., the chemical additives and production process parameters employed for each candidate hydrocarbon residue) needs to ensure that the oil-in-water emulsion fuel has the required droplet size distribution, rheological/hydraulic properties, and both static and dynamic stability. It is also preferred that the resulting oil-in-water emulsion fuel can be blended safely with other emulsion fuels according to the present invention, and/or that are made according to the process of the present invention, but which may have an alternative formulation.

Determination of a desired formulation can be achieved by undertaking a series of matrix screening tests and subsequent optimisation defined within, whereby a sample of a candidate hydrocarbon residue feedstock is used to manufacture a series of emulsions using different process conditions, whilst varying the chemical additives and concentrations to optimise the overall emulsion fuel formulation. The fundamental characteristics of each emulsion batch can be analysed.

One way to characterise the oil in water emulsion is to determine the Droplet Size Distribution (DSD); which provides the distribution profile, median, mean, and span of the hydrocarbon residue once it has been emulsified into the aqueous phase.

The DSD is normally represented as the percentage droplet volume population against size range, from which a number of statistical parameters can be derived. Two common ways of expressing the droplet size distribution include volume or mass moment mean, expressed as D[4,3], and the volume median, which is represented as D[v, 0.5] or $D_{50}$. The "span" is the difference between the largest and smallest droplets/particles. For practical purposes, it is calculated from $D_{90}-D_{10}$, where $D_x$ represents the droplet size at which x % of the droplets have that size. The dimensionless unit, relative span, is often calculated as $(D_{90}-D_{10})/D_{50}$.

Figure 2:
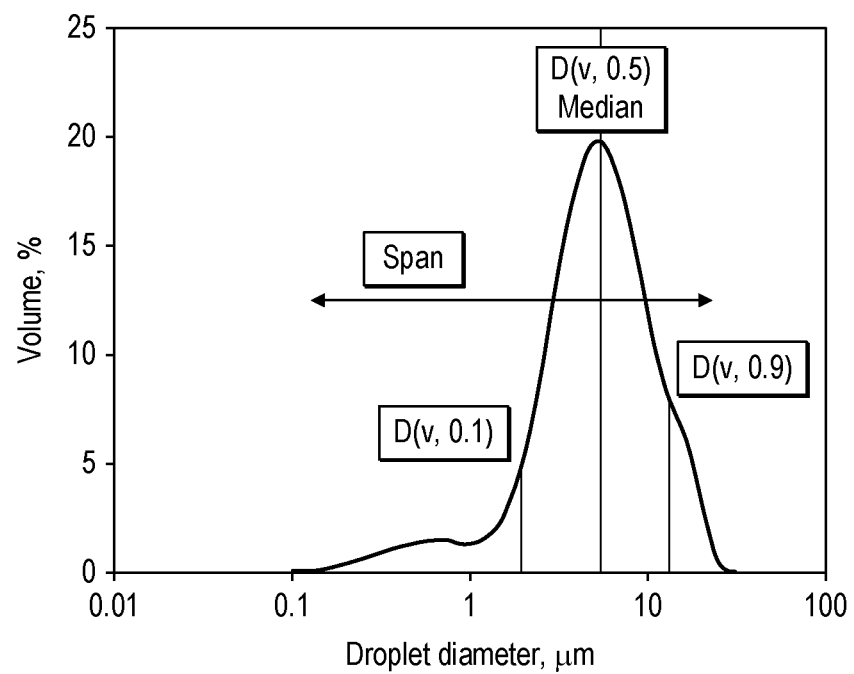
FIG. 2 shows an example of an oil-in-water emulsion fuel droplet size distribution.

When interpreting and evaluating the response of the hydrocarbon residue emulsification to the formulation applied, the differences between these two statistical averages can be advantageously used, because each provides different insights into the droplet size distribution. The volume median droplet size is the size mid-point of the total size distribution or span. The volume mean droplet size is the statistical average of the whole volume distribution, and as such is more sensitive to the presence of droplets with larger size. Accordingly, a decrease in the volume mean droplet size is normally associated with a decrease in the droplet size distribution span, whereas the droplet size distribution can vary in span and the volume median may stay the same. An example of an oil-in-water emulsion fuel droplet size distribution is shown in FIG. 2.

An analytical instrument such as a MALVERN Mastersizer™ can be used to determine the DSD of an oil-in-water emulsion fuel (in the case of MALVERN™ instruments, the size range distribution is determined by standard laser diffraction techniques). In an example analysis, 2.5 ml of 2M formic acid and a 5-8% wt solution of a non-ionic surfactant (e.g., a nonyl phenol or alkyl ethoxylate) are added to 500 ml of clean, finely filtered water. Approximately 0.5 ml of the oil-in-water emulsion fuel sample is mixed with 5 ml of a 2% wt solution of a stabilising agent (such as a fatty alcohol ethoxylate or fatty alkyl diamine) and dispersed under ambient conditions. The purpose of this pre-mixing with stabilising agent is to ensure that the emulsion particle/droplet sizes of the oil-in-water emulsion remain unaltered during the remainder of the analysis process, which involves adding drops of this dispersion to the recirculated 500 ml formic acid/surfactant solution previously prepared until an acceptable obscuration value for the Micro Mastersizer™ is achieved. Typically a measurement cycle of 5 repeats with 2000 sweeps each is then performed to obtain the DSD analysis. Alternative methods for determining droplet size distribution are also available, such as that using a Coulter Counter instrument (which employs the technique of measuring changes in the electrical resistance of a dilute emulsion when a potential difference is applied and the sample is drawn through a microchannel) or by optical image analysis (whereby a microscopic recorded image of the emulsion is analysed using computer algorithm). Similar sample preparation protocols can be used.

The combination of the volume mean droplet size (D[4, 3]) range of from 3 to 15 μm and the proportion of droplets having a size of greater than 125 μm being less than 3 wt %, helps to achieve the static and dynamic stabilities required.

Another parameter that can be used to characterise the oil-in-water emulsion is viscosity (typically measured over controlled shear rate and temperature conditions of 10 to 150 $s^{-1}$ at 50° C.). Oil-in-water emulsions according to the invention can typically contain a high (greater than 60% wt) concentration of hydrocarbon residue. Factors affecting the resulting rheology of such emulsions include;

contact and deformation between droplets due to the relatively 'crowded' packing, which is influenced by the internal (hydrocarbon residue) phase viscosity, and rheological properties of the interstitial continuous (water/additive) phase.

Such concentrated emulsions normally display non-Newtonian behaviour, whereby the viscosity of the emulsion at any given temperature will vary with the applied level of shear. It is possible to model this non-Newtonian behaviour (e.g., using the Power Law model) and hence quantify and characterise the emulsions' rheological behaviour. Such emulsions can also display time dependent rheological behaviour (such as thixotropy) whereby the viscosity will be influenced by how long shear is applied. This can be a fully or semi-recoverable phenomenon, whereby the viscosity will return to its initial value in part or in full over time.

All of these rheological characteristics can be influenced by the type of hydrocarbon residue being used, and the chemical additives applied.

An analytical instrument such as a MALVERN KINEXUS™ or a HAAKE VT550™ Rheometer can be used to determine the rheological properties (including viscosity) of an oil-in-water emulsion fuel. An example of such a measurement includes the use of a parallel plate configuration (using a 40 mm rotational element, set with a 1 mm gap), in which a sample of temperature controlled (e.g. 50° C.) oil-in-water emulsion fuel sample is subjected to shear cycles, ascending and descending between 15-150 s$^{-1}$. The corresponding viscosity values, for example at 20 and 100 s$^{-1}$ on the descending cycle, can then be determined.

Maintaining the viscosity range of greater than 100 to 700 mPas (at 20 s$^{-1}$ and 50° C.), in addition to maintaining the droplet size distribution characteristics mentioned above, helps to achieve the required dynamic and static stability of the oil-in-water emulsion.

Sedimentation

Static stability can be measured by determining sedimentation during centrifugation. In an example of an analysis, a 10 ml emulsion fuel sample is subjected to 2000 g at 50° C. for 30 mins, using a lab scale centrifuge (e.g., Hettich™ Universal 1200). The sample tube is then carefully washed with a 2% solution of a non-ionic surfactant (e.g., a nonyl phenol or alkyl ethoxylate), to remove non-compacted emulsion from the sediment. The washed tubes are then dried in an oven at 105° C. for 2 hours prior to weighing, so that the % wt. of sediment can be calculated.

Sieve Testing

Sieve testing can provide a measure of residue droplets greater than 125 μm in the oil-in-water emulsion, thereby providing an indication of emulsion stability post production. The method can be based on the standard ASTM test methods D4513-85, D4572-89 and D6933, and gives a measure of the amount of free oil residue/non-emulsified material present in the sample. A known weight of approximately 100 g is washed though a 125 μm sieve using a 2% solution of a non-ionic surfactant (e.g., a nonyl phenol or alkyl ethoxylate). The sieve is then dried in an oven at 105° C. for 2 hours prior to weighing, so that the % wt. of retained material can be calculated.

Optimisation

A method for optimising the oil-in-water emulsion formulation can include various sequential stages as follows;

Hydrocarbon residue sample analysis

Matrix formulation screening, emulsification evaluation and (static) stability testing Dynamic stability testing consisting of laboratory and pilot scale testing Accordingly, a number of experimental test protocols have been developed at laboratory and pilot scale to evaluate the characteristics and stability of the oil-in-water emulsion fuel formulations over a range of representative (typical) operational conditions that would be experienced when used as a marine fuel.

Hydrocarbon Residue Sample Analysis

A hydrocarbon residue can be analysed for the properties indicated in Table 7.

This initial analysis is primarily to establish if the hydrocarbon residue meets the requirements of a feedstock for oil-in-water emulsion fuel production, and to provide information on key composition parameters that may impact the chemical formulation required.

The Simulated Distillation (SIMDIST), water and flash point determination give an indication of the general composition of the residue.

The ash content and elemental analysis of the residue, as well as the calorific value determination, help to evaluate the potential combustion performance and resulting environmental emissions.

Aluminium and silica in a fuel can act as abrasives, hence determination of their content is often a specific requirement if the resulting emulsion fuel is to be used within the marine industry, to ensure the integrity of engine operations.

A higher pour point value can indicate that a hydrocarbon residue is more paraffinic (waxy) in composition, which influences the chemical additives to be used in producing an optimum oil-in-water emulsion fuel. For example, for unbranched paraffinic (waxy) hydrocarbons, it is generally useful to employ a primary surfactant having unbranched paraffinic (waxy) hydrocarbon chains. Further techniques such as low temperature rheological analysis, microscopy, etc., can also assist in determining the potential waxy nature of the sample.

TABLE 7

Tests for Hydrocarbon Residues

| Test | Unit | Suggested Method | Relevance |
|---|---|---|---|
| Density | g/ml | ASTM D4052 | Physical Properties/Emulsification |
| Viscosity | cst | Rotation Viscometry | Physical Properties/Emulsification |
| GCV | MJ/kg | ASTM D 240 | Economic Value/Combustion |
| NCV | MJ/kg | ASTM D 240 | Economic Value/Combustion |
| Sulphur | % wt | ASTM D2622 | Compliance/Combustion |
| Nitrogen | % wt | ASTMD5291m | Compliance/Combustion |
| Carbon | % wt | ASTMD5291m | Compliance/Combustion |
| Hydrogen | % wt | ASTMD5291m | Compliance/Combustion |
| Oxygen | % wt | Calc. | Compliance/Combustion |
| Chlorine | mg/kg | U.O.P.779M | Compliance/Combustion/Emulsification |
| Sodium/Calcium | mg/kg | ICP/AAS | Compliance/Combustion/Emulsification |
| Aluminium + Silica | mg/kg | ICP/AAS | Compliance/Combustion |
| Micro Carbon Residue | % wt | ASTM D4530 | Physical Properties/Emulsification |
| Ash | % wt | ASTM D 482 | Compliance/Combustion |
| Flash Point (COC) | degC. | ASTM D 92 | Compliance/Physical Properties |

TABLE 7-continued

Tests for Hydrocarbon Residues

| Test | Unit | Suggested Method | Relevance |
|---|---|---|---|
| Pour Point | degC. | ASTM D 97 | Physical properties/Emulsification |
| TAN | mgKOH/g | ASTM D664 | Chemical Properties/Emulsification |
| TBN | mgKOH/g | ASTM D2896 | Chemical Properties/Emulsification |
| Water | % wt | ASTM D 95 | Chemical Properties/Emulsification |
| SIMDIST | % wt/degC. | HTSD | Chemical Properties/Emulsification |
| Asphaltenes | % wt | IP 143 | Physical Properties/Emulsification |
| Asphaltene colloidal state | $FR_{max}/P_o$ | ASTM D7060 | Physical Properties/Emulsification |

Relatively high TAN/TBN values are an indication of an increased level of heterogeneous/ionic chemical functionality in the chemical composition of the hydrocarbon residue, which is often associated with higher asphaltenes content. As a number of the chemical additives used are ionic in nature, the level of indigenous ionic species present in the residue can affect the optimum combination and concentration of additive chemicals used in the oil-in-water emulsion fuel formulation.

Higher viscosities indicate a need for elevated temperatures for effective emulsification.

Higher densities indicate a need for the use of (or increased use of) polymeric stabiliser agents in the emulsion formulation to offset the density difference between the hydrocarbon residue and aqueous phases.

A high level of alkaline metals (e.g., Na, Ca) and/or halogens (e.g., Cl, which is an undesirable contaminant for fuel combustion emissions) could indicate the presence of salts in the hydrocarbon residue. The presence of such salts can lead to an undesirable osmotic droplet swelling (thickening) process, resulting in a significant increase in viscosity over time. This can be corrected by balancing the ionic content of the hydrocarbon residue and aqueous phases.

Matrix Formulation Screening

Figure 3:
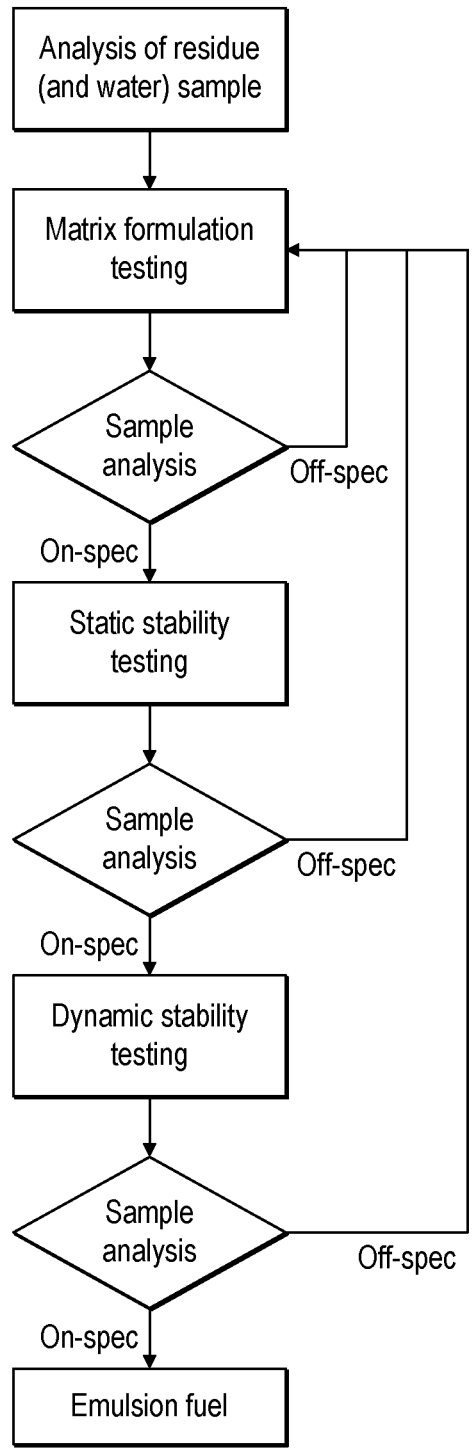
FIG. 3 shows a schematic of the matrix formulation and testing process.

'Matrix' formulation testing can be used to optimise the oil-in-water emulsion formulation. It is an iterative process. As all the parameters being evaluated are interdependent, optimisation of the emulsification formulation requires determination of the correct balance of all the parameters and variables involved. In this way the response of the candidate hydrocarbon residue to the different process conditions and additives used is evaluated against the target specification. A guideline to this approach to determine the optimum formulation follows, and is illustrated in FIG. 3.

Initial Hydrocarbon Residue Emulsification

The first step in the evaluation of the potential to emulsify a refinery residue is to calculate the required temperature to yield a hydrocarbon residue viscosity of 300 to 500 cSt. The temperature of the water/additive phase required is then calculated, which would result in a hydrocarbon residue/water interfacial temperature at which the residue viscosity is less than 10,000 cSt (after correcting for phase ratio and relevant heat capacities), while ensuring the other temperature requirements of the water (such as to avoid boiling, thermal and phase stability of the additives) are met.

Example 1

The hydrocarbon residue viscosity at 100° C.=1450 cSt. When heated to 130° C. this reduces to 260 cSt. Heating the additive aqueous solution to 55° C. will result in an estimated interfacial temperature of 95° C. (with a hydrocarbon residue content of 70%, taking into consideration hydrocarbon residue/aqueous phase heat capacity values), which corresponds to a hydrocarbon residue viscosity of approximately 2,000 cSt at the residue/water interface.

Example 2

Hydrocarbon residue viscosity at 100° C.=14670 cSt, when heated to 155° C. this reduces to 400 cSt. Heating the additive solution to 70° C. will result in an estimated interfacial temperature of 115° C. (with a hydrocarbon residue content of 70%, taking into consideration hydrocarbon residue/aqueous phase heat capacity values), which corresponds to a residue viscosity of approximately 4,300 cSt at the residue/water interface.

With these estimated residue and water phase temperatures, a series of emulsion production tests at laboratory scale can be undertaken using a series of generic 'benchmark' formulations and conditions (e.g. as shown in Table 8) that represent a starting point for further evaluation and optimisation.

TABLE 8

Generic formulation examples for initial emulsification testing

| Component | Value |
|---|---|
| Primary Surfactant | 0.10 to 0.30% wt. |
| Secondary Surfactant | 0.30 to 0.60% wt. |
| Polymeric stabiliser | 0.03 to 0.08% wt |
| pH adjustment with organic acid | 4.5 to 3.0 |
| Residue Content | 66 to 70 wt % |
| Residue temperature | Corresponding to a residue viscosity of 300 to 500 cSt |
| Water phase temperature | Value which gives an interfacial temperature during emulsification <10,000 cSt |
| Mill Speed | Mid-range, ca 8000-10000 rpm |

For the preparation of the aqueous phase containing the additives, the following procedure can be used:

The volume of water to be used for the preparation of the test formulation is heated to between 50 to 70° C.

The required amount of polymeric stabiliser is added to the hot water and mixed until completely dissolved.

Using the organic acid, the pH of the solution is adjusted to be within the range 3 to 4.5.

At this stage of the preparation, the required amount of the secondary surfactant (if included in the formulation) is added and the water phase is mixed to ensure the additives are completely dissolved.

This is followed by the addition of the required amount of the primary surfactant and the water phase is mixed while the pH is adjusted using further organic acid until the required pH is achieved. This mixing continues until all the additives are completely dissolved and activated.

Figure 4:
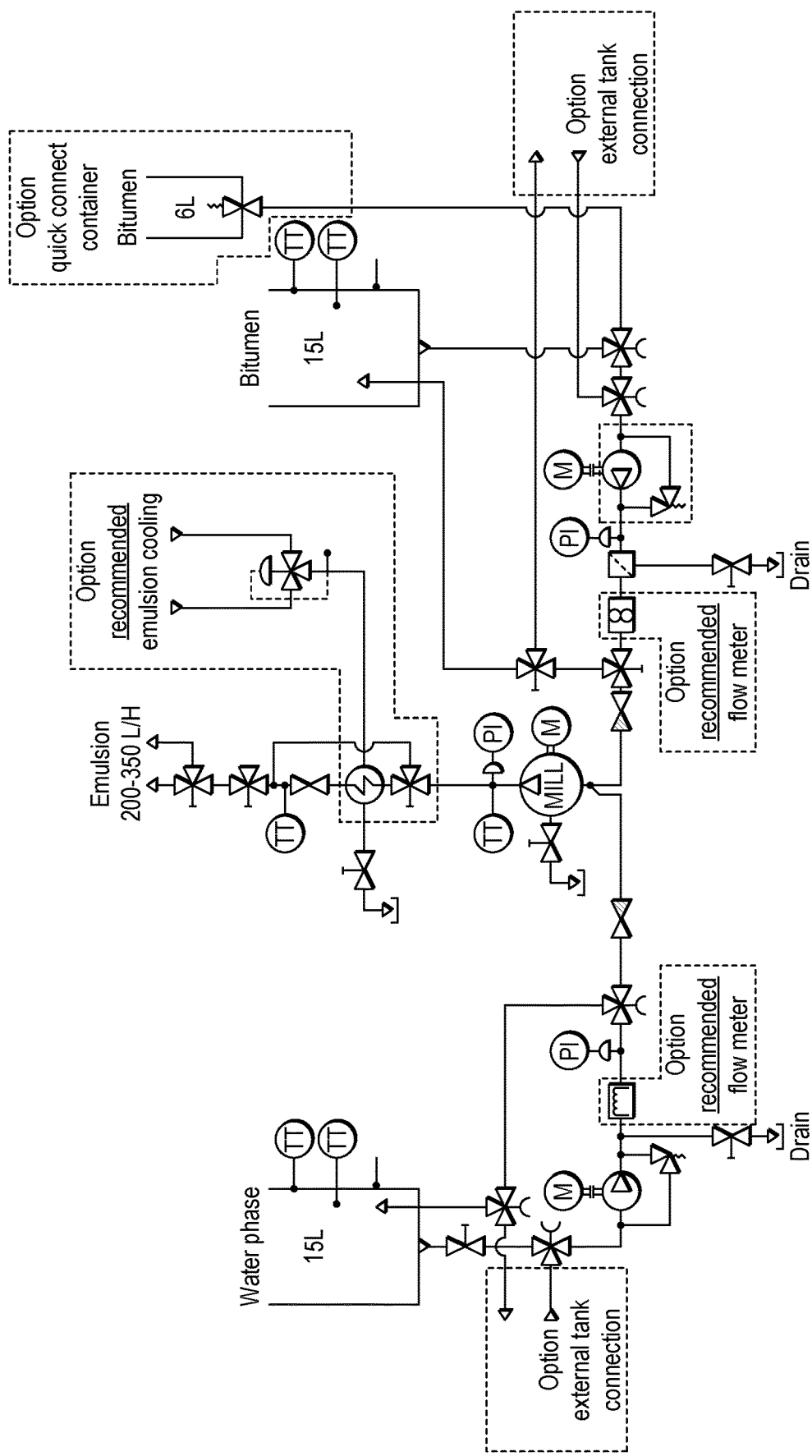
FIG. 4 shows a diagram of an example laboratory scale colloidal mill emulsification system, for the production of test formulation samples.

The aqueous phase is then transferred to a laboratory scale colloidal mill system (such as the DEMINOTECH™ SEP-0.3R Emulsion Research Plant which is capable of producing emulsions at a maximum capacity of 350 l/h, see FIG. 4). A quantity of the residue feed stock for evaluation is then introduced into the system and heated to the required temperature (as indicated above).

The test emulsion can then be prepared using the following procedure;

Flow of cooling water to the system outlet heat exchanger is started.

Pumping of the prepared water phase through the system via the colloidal mill is started.

The mill is switched on and a suitable mid-range speed selected (e.g., 9000 rpm for the SEP-0.3R system). The back pressure on the system is adjusted to approximately 2 bar.

Once steady flows and temperatures are achieved, the hydrocarbon residue pump is started at a low flow rate, and steadily increased until the required flow rate is achieved (e.g., to give a final hydrocarbon residue content in the emulsion). The backpressure of the system is adjusted to maintain a level of approximately 2 bar. The flow rate of water to the final heat exchanger is adjusted to ensure the emulsion is flowing at the outlet of the system at a temperature less than 90° C.

Once steady state operation of the system is achieved (i.e., in terms of flow rates, temperatures and pressures) a sample of the oil-in-water emulsion is taken for testing and analysis.

To stop production pumping of the residue through the system is stopped, and flow of the water phase maintained to flush the system through.

For the further evaluation and optimisation process the operating procedure of the laboratory scale colloidal mill system will be the same, with the required process and formulation variables being adjusted accordingly.

The principle of the production procedure for the manufacture of an oil-in-water emulsion fuel on a large scale using a continuous in-line plant will be the same as described above.

The analysis of these test emulsion preparations provides an indication as to the potential of a candidate hydrocarbon residue to be used as a feedstock for the production of the oil-in-water emulsion fuel by the process described using 'generic' formulation and conditions. Based on the results of these tests, further formulation matrix testing can be carried out if necessary to fine-tune and optimise the response of the residue to emulsification and subsequent stability testing, focusing on specific aspects and variables.

Selection of Primary Surfactant

In the context of an oil/water emulsion system, surfactants can generally be described as molecules that have hydrophilic (water liking) and hydrophobic (oil liking) components. The role of the primary surfactant is to reduce the surface tension at the hydrocarbon residue/water interface such that the surface can be broken up to form droplets. The primary surfactant acts to stabilise the droplet (e.g., by charge density in the case of ionic surfactants) and prevent them from re-coalescing. In order to do this, the hydrophobic part of the primary surfactant molecule must have sufficient affinity for the hydrocarbon residue in order to be fixed (i.e., anchored) at the hydrocarbon residue/water interface. This will depend on the characteristics of the surfactant and the residue alike.

Use of an effective primary surfactant that has sufficient affinity and stabilising properties for the residue results in an emulsion with a smaller average droplet size and a narrower droplet size distribution range. This acts to increase the viscosity of the resulting emulsion, due to its geometrical effect on droplet packing within the emulsion system. The ability to have effective control over droplet size distribution during the emulsification process by influencing, for example, the concentration and pH of the primary surfactant is also a desirable property. In this way, a balance between efficiency of emulsification and required droplet size/rheological properties can be achieved with the correct choice of primary surfactant type.

Figure 5A:
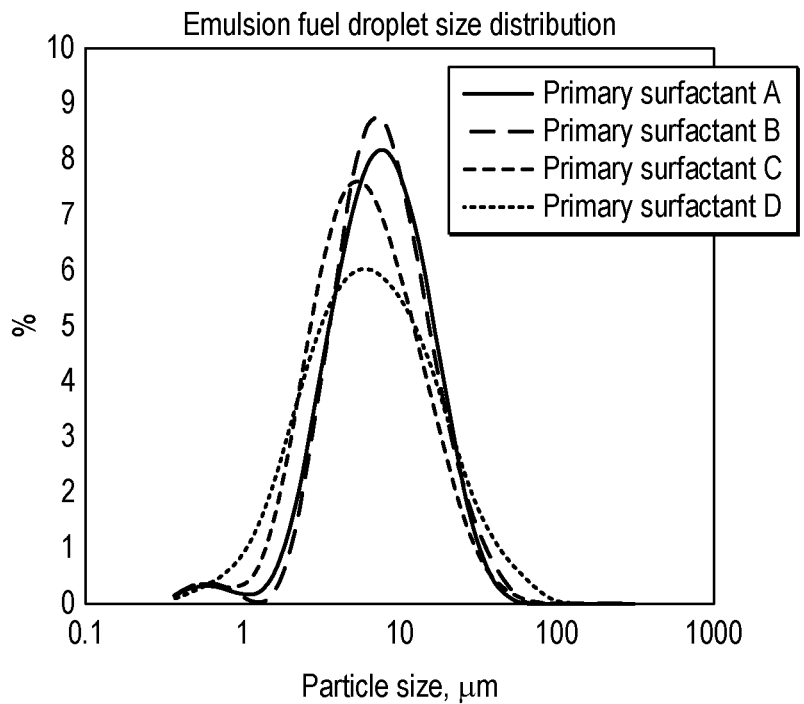
FIGS. 5a and 5b show the effect of primary surfactant type on oil-in-water emulsion characteristics.
Figure 5B:
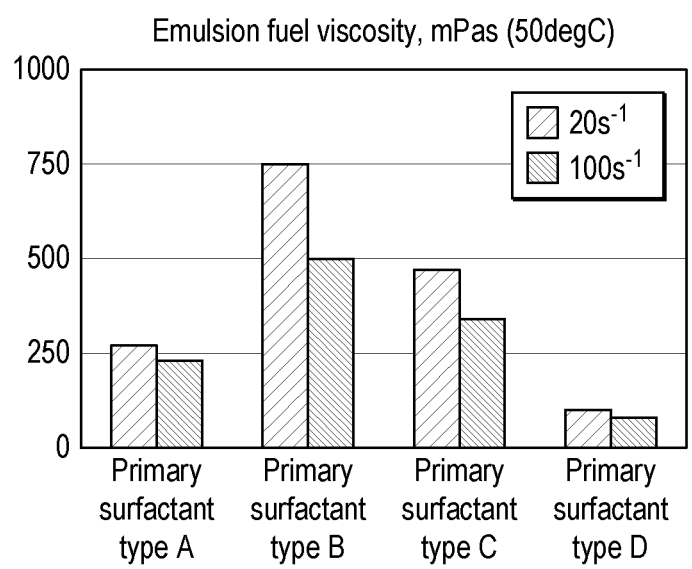

Examples of the effect of primary surfactant on droplet size distribution and viscosity of the resulting fuel emulsion characteristics are given in FIGS. 5a and 5b.

The suitability of primary surfactants is based at this stage on achieving the manufacture of an oil-in-water emulsion fuel with an average droplet size less than 25 μm (D[4,3]), a distribution that has a 90% droplet distribution less than 50 μm (D[v, 0.5]) and a relative span less than 3.5, whilst maintaining a viscosity less than 500 mPas (at 20 s$^{-1}$, 50° C.), using the method for measuring droplet size distributions given above. Further reduction of viscosity can be achieved by other parameters evaluated at a later stage in formulation matrix testing.

To start the process of optimising the oil-in-water emulsion fuel formulation, testing of the primary surfactants is carried out with an initial concentration range of 0.10 to 0.60% wt adjusted to a pH value of 3 to 4.5, without the addition of the secondary surfactant at this stage, since the influence of this additive component is optimised in a later stage. Any polymeric stabiliser is included, the estimated concentration range of which is be based on the density of the hydrocarbon residue. The emulsification and resulting emulsion droplet size distribution can be varied to achieve the required range, for example by;

increasing or decreasing the emulsification mill speed, which will tend to decrease or increase respectively the average droplet size, thereby increasing or decreasing respectively the viscosity increasing or decreasing the concentration of the primary surfactant, which will tend to decrease or increase respectively the average droplet size, thereby increasing or decreasing respectively the viscosity.

Any primary surfactant failing to produce an oil-in-water emulsion or that forms an oil-in-water emulsion that does not show the above variations in viscosity with mill speed or primary surfactant concentration, is discarded at this stage of the formulation tests.

Optimisation of Formulation pH

Figure 6:
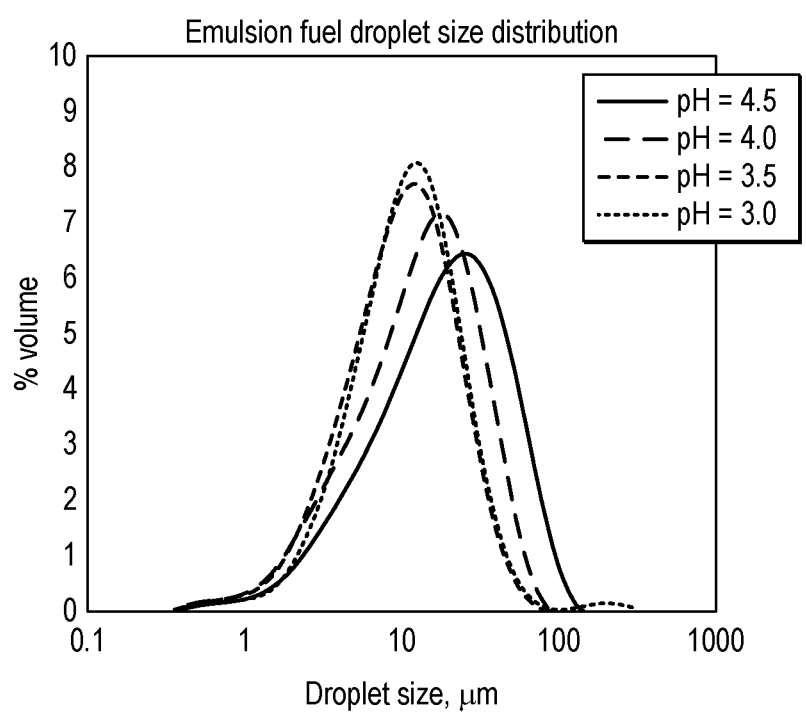
FIG. 6 shows the effect of pH on emulsification.

The next parameter to be optimised is the pH of the aqueous phase during manufacture. A further series of formulation matrix tests is undertaken using the suitable primary surfactants, and varying both the concentration of the surfactant and the addition of acid being tested to achieve a range of pH values between pH 2 and 6. The analysis of the manufactured test batches can include droplet size distribution, viscosity, sedimentation, sieve test and shake table test as indicated above. Examples of the effect of pH on the resulting fuel emulsion characteristics are given in FIG. 6 for a fixed amount of primary surfactant.

The optimum pH is the value at which the lowest average droplet size and viscosity can be achieved that fall within the limits according to the invention. At the same time, static stability must be acceptable as determined by sedimentation, sieve test and shake table results over a nominated period of time (e.g., four weeks at this stage of the evaluation).

Polymeric Stabilising and Flow Improving Agent

Figure 7A:
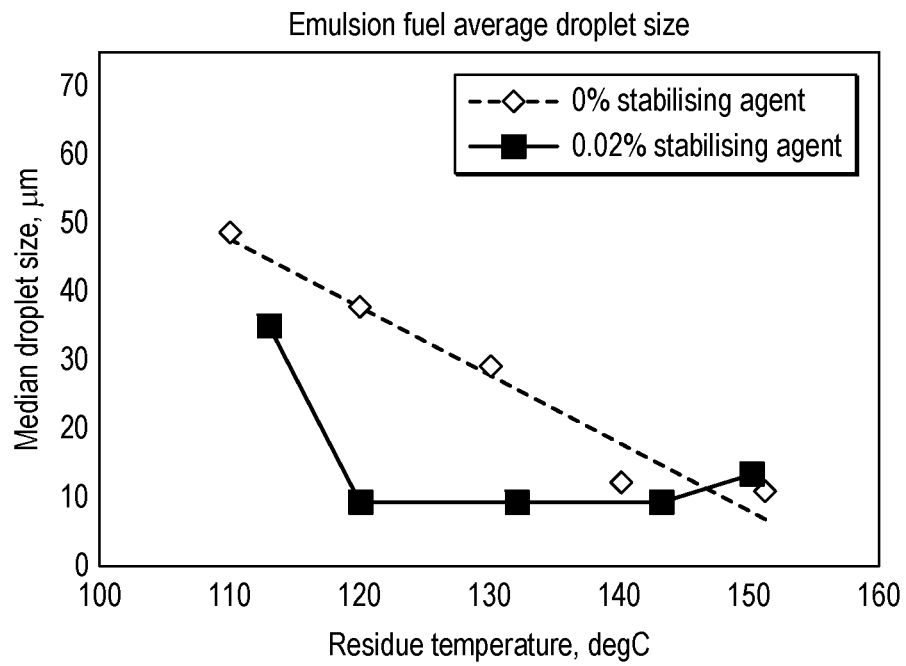
FIGS. 7a and 7b show an example of effect of stabilising and flow improvement agent on emulsion properties.
Figure 7B:
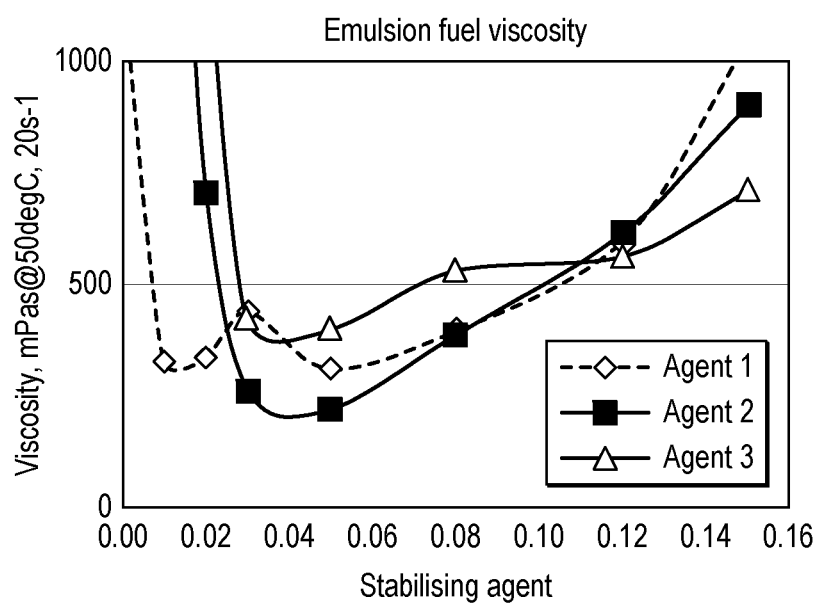

The selection and use of a polymeric stabilising and flow improving agent is based on its interactions with the other chemical additives. The polymeric agent has the potential to influence droplet size distribution, improve (lower) the viscosity of the final oil-in-water emulsion and enhance the stability of the fuel. This is achieved by changing the density differential between the hydrocarbon and aqueous phases and through the formation of a low yield gel structure as indicated earlier. Examples of the effect of polymeric stabilising and flow improvement agent on the resulting fuel emulsion characteristics are given in FIGS. 7a and 7b.

Introduction of the Secondary Surfactant

Once the selection and basic behaviour of the primary surfactant with the optional polymeric agent is established, a further series of formulation tests are undertaken with the inclusion of secondary surfactant if required, and at a concentration within the range indicated in Table 4 or Table 8.

Figure 8:
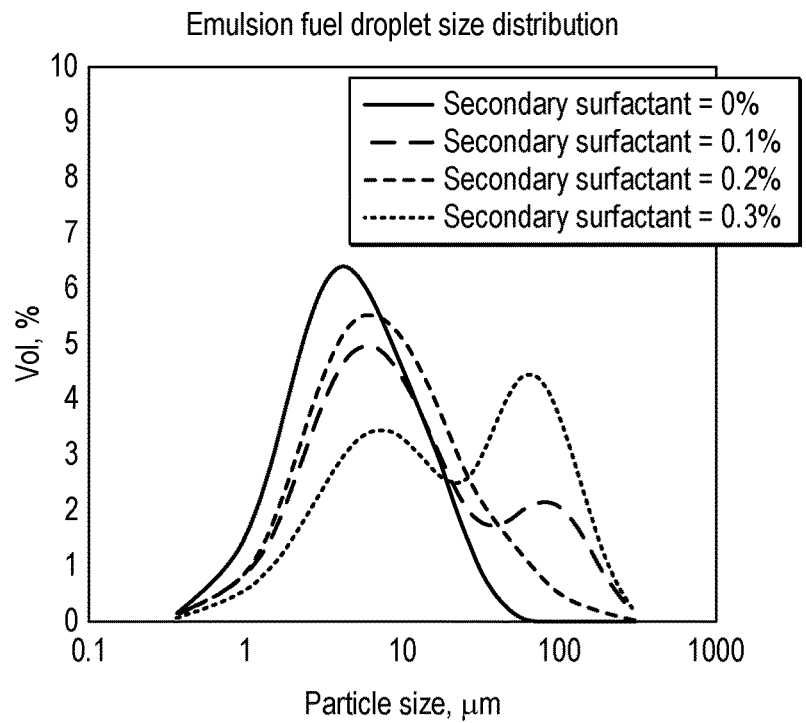
FIG. 8 shows an example of the influence of secondary surfactant inclusion in the emulsion formulation.

The role of the secondary surfactants is to provide a high degree of dynamic stability. Its inclusion in the formulation is usually required, for example, when the emulsion fuel is intended for use in engines (e.g., for propulsion in ships), where the fuel handling conditions are more severe in terms of pumping, shearing and large changes in pressure. Typically secondary surfactants will have a larger hydrophilic group, and will thereby impart a degree of steric stabilisation into the emulsion system. The secondary and primary surfactants compete for the interface during the emulsification process; which will be influenced by their relative concentrations (see FIG. 8). Secondary surfactants are not as efficient as an emulsifier as the primary surfactant, so their interfacial displacement of the primary surfactant will result in a tendency to broaden the emulsion droplet size distribution (which will also have the effect of lowering the viscosity of the system). Again, the balance between the components of the required formulation and final emulsion fuel characteristics can be optimised.

Further Optimisation of Temperatures and Mixing (Mill) Speed

Figure 9:
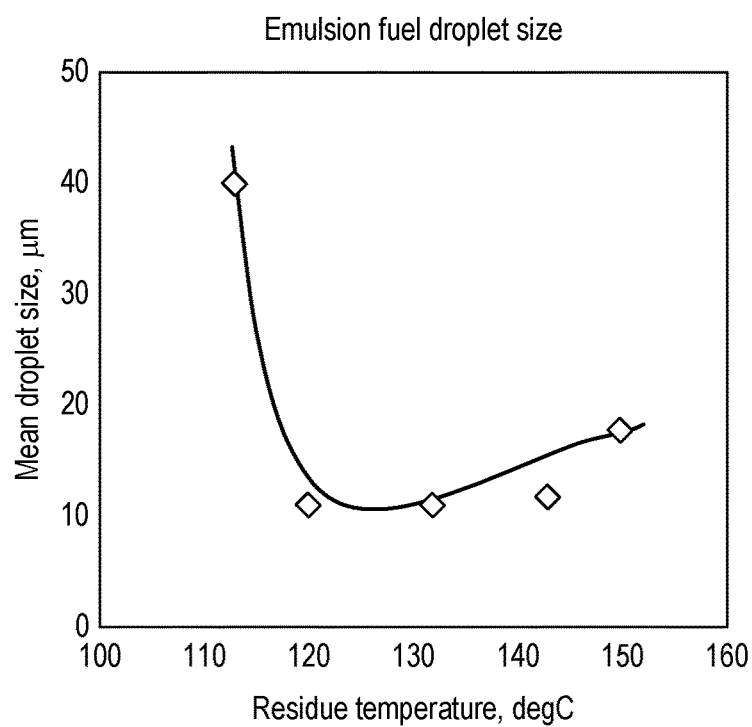
FIG. 9 shows the effect of hydrocarbon residue temperature (with fixed water phase temperature) on emulsification.

With the presence of the primary, and the optional secondary surfactants and optional polymeric stabiliser, a series of matrix formulation tests can be undertaken to fine-tune the balance between the hydrocarbon residue and aqueous phase temperatures during the emulsification process at the optimum identified pH range. An example of the effect of hydrocarbon residue temperature balance with fixed aqueous phase temperature on the resulting droplet size distribution of the oil-in-water emulsion fuel is provided in FIG. 9.

Figure 10A:
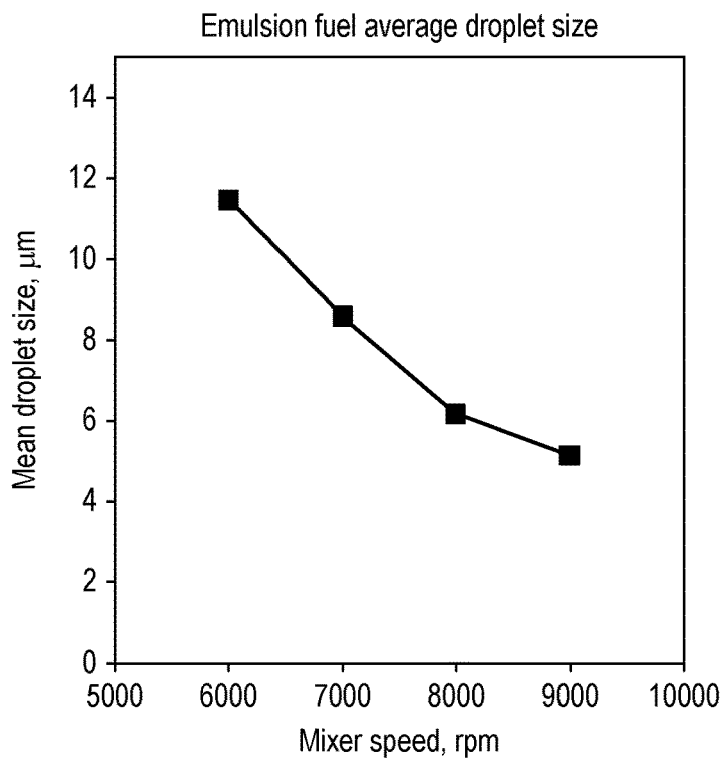
FIG. 10 shows the effect of mill speed on emulsification, and resulting droplet size on viscosity.
Figure 10B:
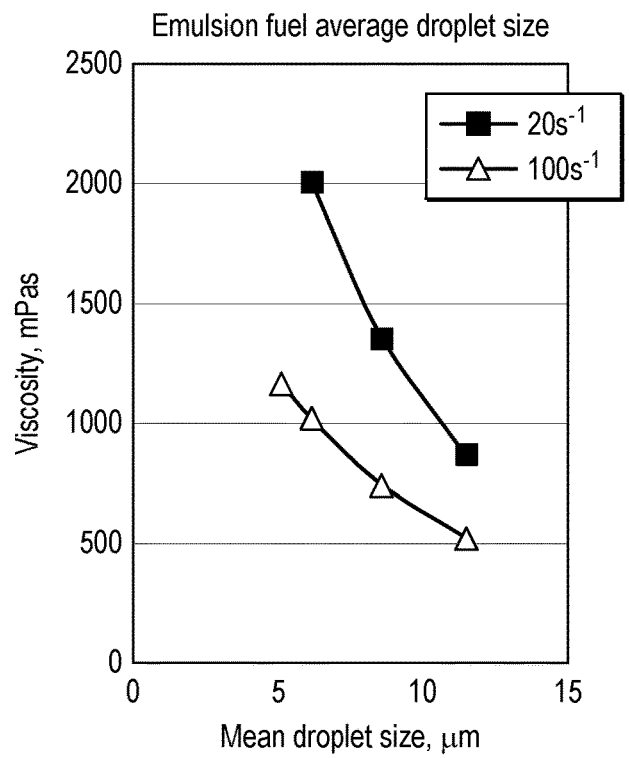

The optimum mixer or milling speed can be determined at this stage, since with increased speed more energy is imparted into the emulsion system during manufacture which will tend to decrease the average droplet size and distribution span, thereby increasing viscosity. Examples of the effect of mill (mixer) speed on the resulting fuel emulsion characteristics are given in FIGS. 10a and 10b.

Evaluation of Optimum Emulsion Residue Content

Figure 11:
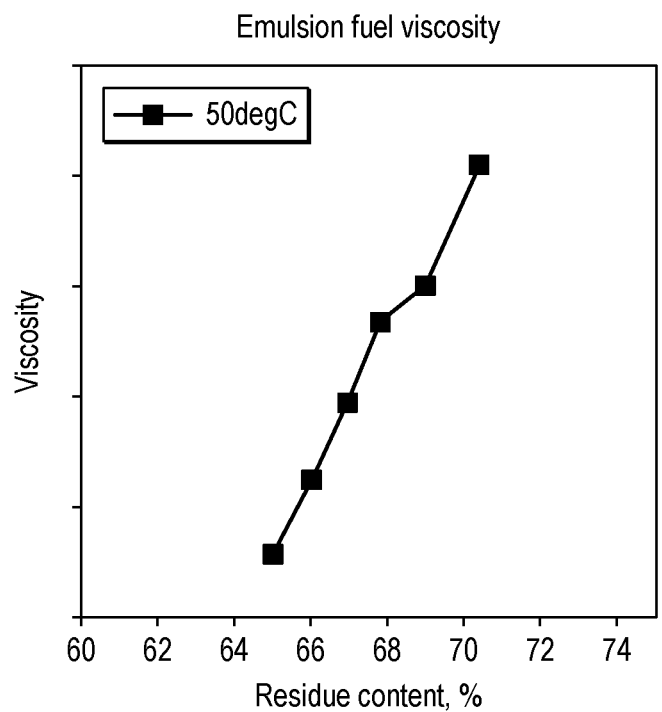
FIG. 11 shows the effect of residue and water content on emulsification.

The predominant influence of the hydrocarbon residue content on an oil-in-water emulsion will be on viscosity. As the internal phase of the emulsion (i.e., the hydrocarbon residue content) is increased, the viscosity will also increase, particularly at concentrations greater than 60 wt %. An example of the effect of residue content on the resulting oil-in-water emulsion characteristics is given in FIG. 11.

It is preferred to have as much hydrocarbon residue in the emulsion fuel as possible so as to maximise its energy content, while still retaining the other required characteristics to ensure a stable emulsion.

Optimisation of Emulsion Droplet Size Packing Density

Figure 12:
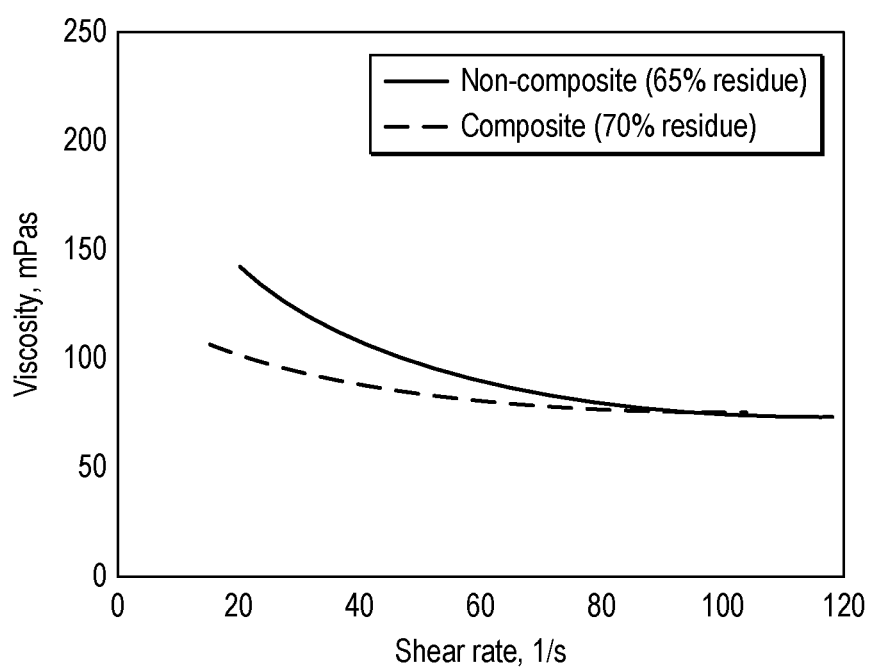
FIG. 12 shows the effect of the influence of composite emulsion manufacture.

Optimisation of the packing density of droplets using composite emulsion technology can reduce viscosity. A composite emulsion is one that is manufactured from two or more component emulsions of differing droplet size distributions. By their correct combination, it is possible to get improved packing of smaller droplets with larger ones allowing either a decrease in viscosity for a given dispersed (hydrocarbon residue) phase or an increase in the hydrocarbon residue (i.e., energy) content without significantly increasing viscosity. This can arise due from a reduced tendency for inter-droplet impaction and deformation during flow, leading to a reduction in viscosity. An example of the influence of composite emulsion formulation on viscosity is shown in FIG. 12. This is another factor that can be used in the formulation of emulsion fuels to obtain the best optimisation of required characteristics.

Laboratory and Pilot Scale Dynamic (Handling) Stability Testing

Candidate formulations resulting from the matrix screening and static stability requirement in the specification can be subjected to further dynamic stability testing.

Dynamic stability is important because an emulsion fuel can be subjected to heating as well as high shearing and turbulence during pumping and transportation.

Figure 13:
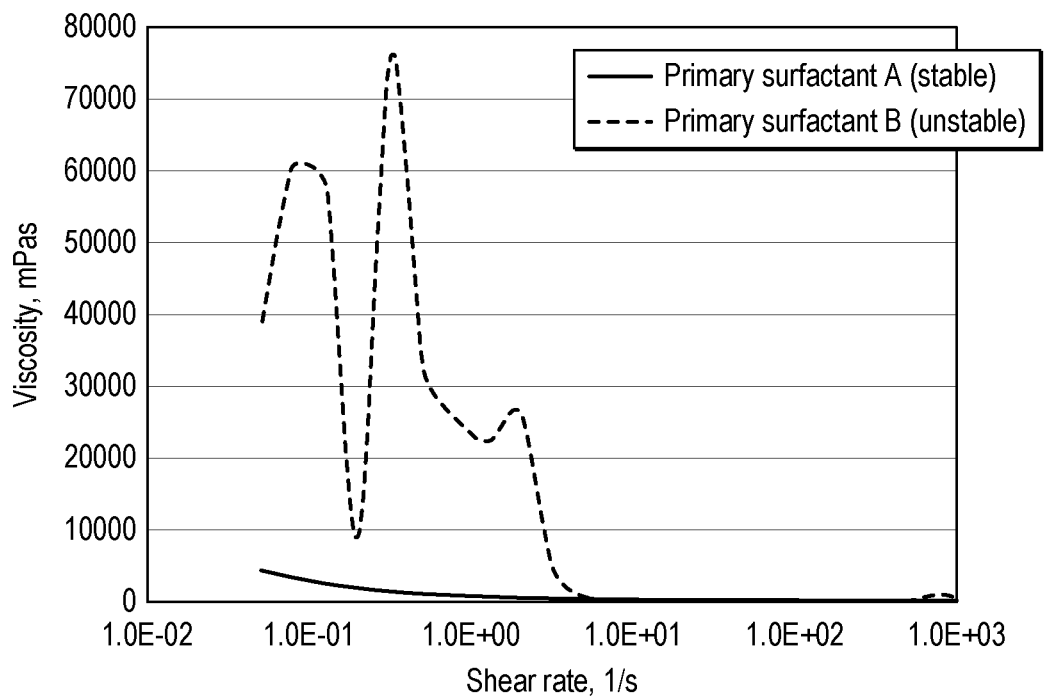
FIG. 13 shows the effect of dynamic stability testing demonstrating good shear stability (with primary surfactant A) and poor shear stability (with primary surfactant B)

A number of devices can be used to measure dynamic stability (such as controlled speed mixers or rheometers/viscometers) that can impart controlled shear, under temperature controlled conditions, to a sample of an oil-in-water emulsion fuel. Such test conditions are used to make both qualitative and quantitative judgements of the change in emulsion fuel characteristics, particularly those relating to changes in droplet size distribution. FIG. 13 shows the effect that primary surfactant type can have on dynamic (shear) stability using a rheometer test protocol. An analytical instrument such as a MALVERN KINEXUS or a HAAKE VT550 Rheometer can be used to determine the dynamic stability of an emulsion fuel. An example of such a measurement involves using a parallel plate configuration (using a 40 mm rotational element, set with a 1 mm gap). A sample of temperature controlled (50° C.) emulsion fuel is subject to a shear cycle, in which the element revolves at a rate ascending from 0.5-1000 s$^{-1}$. If the shear/stress characteristics observed during such a test show typical shear thinning characteristics (i.e. a steady reduction in viscosity with increasing shear, with a 'n' value typically within the range 0.7 to 0.95 as determined by the Power Law model), the sample is expected to have a high potential for good dynamic stability.

Another example of a laboratory based method for the evaluation of dynamic stability is the Shake Table test. The test gives an assessment of static/dynamic stability by measuring the comparative amount of residue droplets/particles greater than 125 μm in the bulk emulsion after a 100 mg sample of the emulsion is subjected to a controlled amount of agitation for 24 hours at fixed temperature (40° C.), shaking frequency (3.3 Hz/200 rpm) and shaking stroke setting (18 mm) on a shake table apparatus such as the JulaBo SW-20C.

Figure 14:
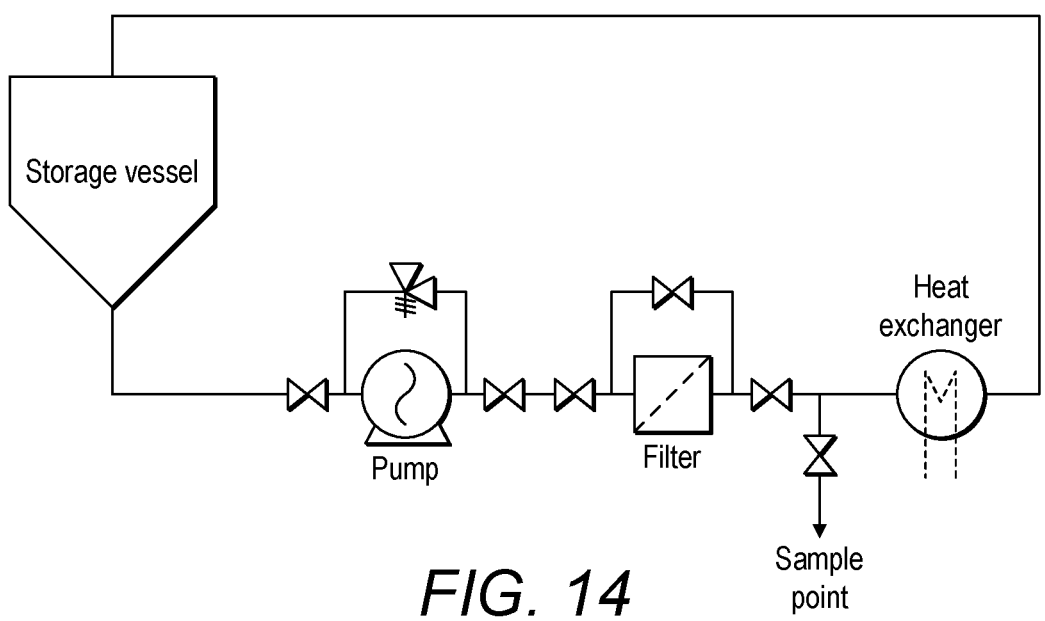
FIG. 14 shows a schematic diagram of an emulsion pilot scale pump test rig.

A pump testing method can also be used, for example using a pilot scale pump testing rig as shown in FIG. 14.

Generally, the method comprises:
  providing an oil-in-water emulsion;
  recirculating the oil-in-water emulsion in a recirculation loop; and
  analysing the oil-in-water emulsion at a first time before recirculation, and at a predetermined time after recirculation; and comparing the samples taken to determine the oil-in-water emulsion's dynamic stability.

The temperature at which the recirculation is carried out is dependent on the viscosity of the emulsion, although it is typically in the range of from 40 to 90° C., for example 40 to 60° C., and typically at 50° C.±10% (i.e. 50° C. or in the range of from 45 to 55° C.).

The emulsion used is preferably recirculated in the range of 25 to 50 times per hour. Thus, for example, for a 10 kg sample, it is preferably recirculated around the recirculation loop at a rate of 250 to 500 kg per hour. Preferably, the range is 31 to 45 times per hour (e.g. 310 to 450 kg per hour for a 10 kg sample). In one example, the rate is 37 times per hour±10%, i.e. 37 times per hour, or in the range of from 33.3 to 40.7 times per hour. For a 10 kg sample, this would equate to 370 kg per hour±10%, i.e. 370 kg per hour, or in the range of from 333 to 407 kg per hour for a 10 kg sample).

The mass of oil-in-water emulsion sample compared to the internal volume of the recirculation loop is preferably in the range of from 2.0 to 5.0 kg/L, for example in the range of from 2.5 to 4.6 kg/L. In one example, the ratio is 4.2 kg/L±10% (i.e. 4.2 kg/L or in the range of from 3.78 to 4.62 kg/L).

The recirculation is carried out over a predetermined period of time, for example in the range of from 5 minutes to 8 hours, typically from 5 minutes to 180 minutes, such as in the range of from 20 to 120 minutes or in the range of from 20 to 40 minutes. In one embodiment, the pre-determined period of time is 30 minutes±10% (i.e. 30 minutes, or in the range of from 27 to 33 minutes).

The particle size distribution of the emulsion (D[4,3]) is analysed during the recirculation before and after the pre-determined period of time. One or more intermediate determinations can optionally be taken if required. For example, the predetermined period of time for the test can be 30 minutes, with particle/droplet size distribution being determined before recirculation and at 30 minutes after recirculation commences. Optionally intermediate analysis can take place, for example at 10 and 20 minutes after recirculation commences.

The dynamic stability test is preferably conducted at least 12 hours after the production of the emulsion, and at any other time during the expected lifetime of the emulsion. For example, for a marine fuel, the expected storage time can be in the range of 3 to 9 months. For power applications, the storage time is typically 1 to 3 months. Therefore, the test is conducted in the range of from 12 hours and up to 9 months after production, for example from 12 hours up to 3 months or from 12 hours up to 1 month after production.

Recirculation can take place with a back-pressure. Typically, the back-pressure of the recirculation is at least 2 barg (bar-gauge), for example in the range of from 2 to 10 barg or from 5 to 10 barg, such as in the range of from 7 to 9 barg, for example 8 barg±10%.

Particle or droplet size distribution can be measured by routine means, for example by light scattering techniques. They can be carried out on-line, without the need for sample extraction. Alternatively, samples can be removed from the recirculation loop and analysed off-line.

For an oil-in-water emulsion to be considered to have acceptable dynamic stability for use, for example, as a marine fuel, the change in average particle size (D[4,3]) after the pre-determined period of time is less than 0.3 µm. Typical conditions of such a test are a temperature of 50° C., a recirculation rate (on a mass basis) of 37 h$^{-1}$, a total mass of sample to recirculation volume ratio of 4.2 kg L$^{-1}$, and a back pressure of 8 barg. Optionally, any or all of these parameters can be within±10% of those stated. The sample time is 30 minutes, optionally with two intermediate samples at 10 and 20 minutes after recirculation commences. A suitable sample size is 10 kg.

Optionally, if the change in average particle size after the pre-determined period of time is acceptable, recirculation can be continued through a filter. Thus, if an oil-in-water emulsion has sufficient dynamic stability after the initial test, a more robust test can be carried out. The filter is typically a 150 µm to 500 µm filter (100 mesh to 35 mesh), for example a 150 µm (100 mesh) or 500 µm (35 mesh) filter. The test conditions with filter can be the same or different, and are typically as set out above. Preferably, the test conditions with the filter are the same as the test conditions without the filter.

The change in average particle size (D[4,3]) before and after the pre-determined time of recirculation in the presence of the filter is also preferably less than 0.3 µm.

In another embodiment, the emulsion is pre-conditioned by recirculating the emulsion for an initial period of time before the start of the test and under the same conditions, without passing through a filter. The preconditioning time is typically in the range of from 5 to 60 minutes, and is preferably in the range of from 10 to 30 minutes. The emulsion is then diverted through a filter, and the dynamic stability test conducted in the presence of the filter.

With reference to FIG. 14, one embodiment employs a system comprising a sample storage vessel large enough the hold 10 kg (approximately 10 litres) of test sample.

The pump recirculation loop is constructed from 25 mm ID pipework with a total loop length of approximately 4.7 m (giving a recirculation loop capacity of approximately 2.4 litres). The pump is a triple screw-pump rated to give a flow rate of approximately 370 kg/h (i.e. 37 times the emulsion volume per hour). The filter unit (e.g., simplex basket filter) is fitted with changeable filter elements typically of 150 or 500 µm size.

The candidate emulsion is pre-heated to the required temperature (i.e., 50° C., optionally±10%) and then transferred to the pump rig storage vessel.

The storage vessel is then opened to the pumping loop, which floods the suction of the pump.

The pump is started and recirculation back to the storage vessel is established at the required flow rate.

The emulsion is then pumped around the system, initially by-passing the filter unit, at a controlled flow rate while the test temperature is maintained by the use of the hot water in-line heat exchanger (a plate type heat exchanger). The back-pressure on the system is adjusted to 8 bar.

Samples are taken at intervals of 10, 20 and 30 minutes for analysis (to determine droplet size characteristics and viscosity), in order to measure the impact of pumping on the heated oil-in-water emulsion fuel.

After the 30 minute sample is taken, the flow of test emulsion is diverted through the filter unit. Periodic samples are again taken for analysis (usually droplet size distribution and viscosity) at 10, 20 and 30 minute intervals to measure the additional impact of filtration on the oil-in-water emulsion fuel.

Figure 15A:
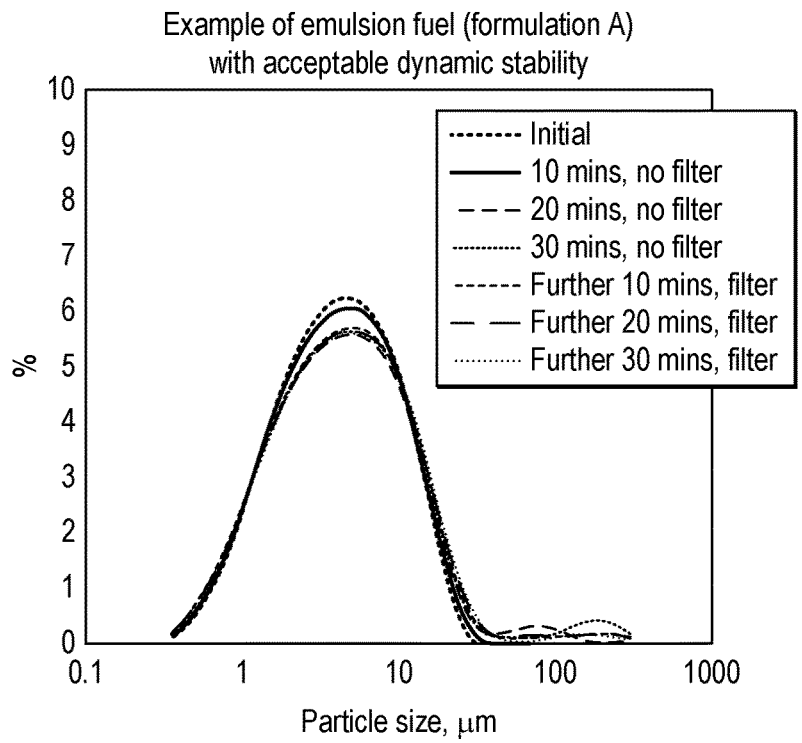
FIGS. 15a and 15b show results of dynamic stability from emulsion pump testing.
Figure 15B:
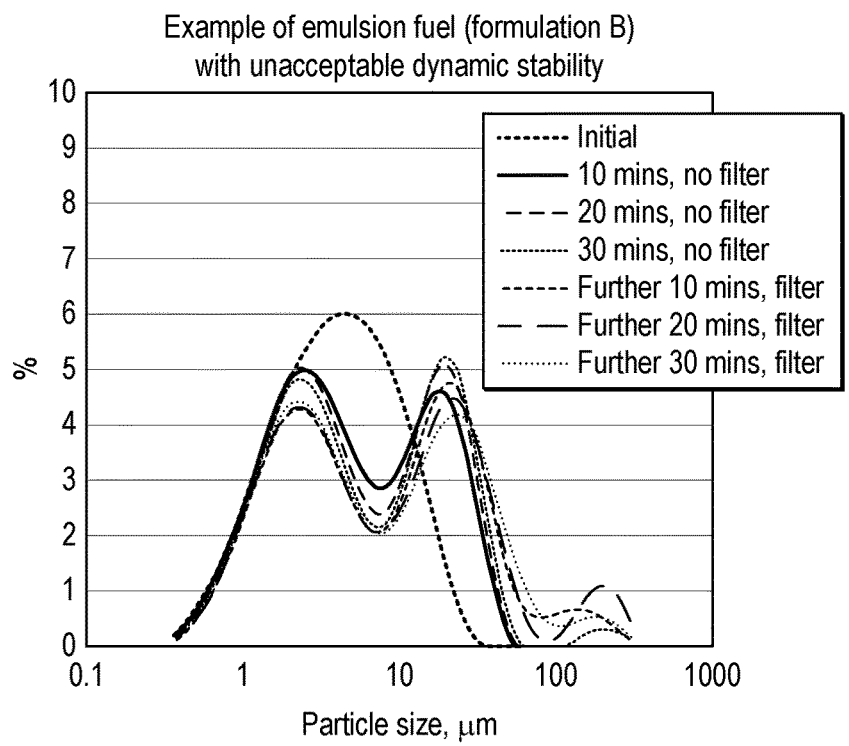

Because the same volume of oil-in-water emulsion fuel is re-circulated through the system many times during the test, it is considered a robust test of the emulsion's dynamic stability, and its ability to withstand the handling conditions that the fuel could experience during operational use. A range of pump designs can be tested with this system to match that envisaged in the use of the oil-in-water emulsion fuel as applicable. Examples of the results from the dynamic stability pump testing are in shown in FIGS. 15a and 15b. These data show the dynamic stability characteristics of two formulations as detailed in Table 9. The dynamic stability is considered acceptable if the emulsion retains a discrete droplet size distribution (i.e., the % wt. of particle above 125 µm remains less than 3%, and the relative span of the distribution is less than 5.0. On comparison between these two specific formulations it can be seen that the formulation designated 'B' has a level of secondary surfactant that is too low. When this is increased (as in Formulation 'A'), acceptable dynamic stability is observed.

Figure 16:
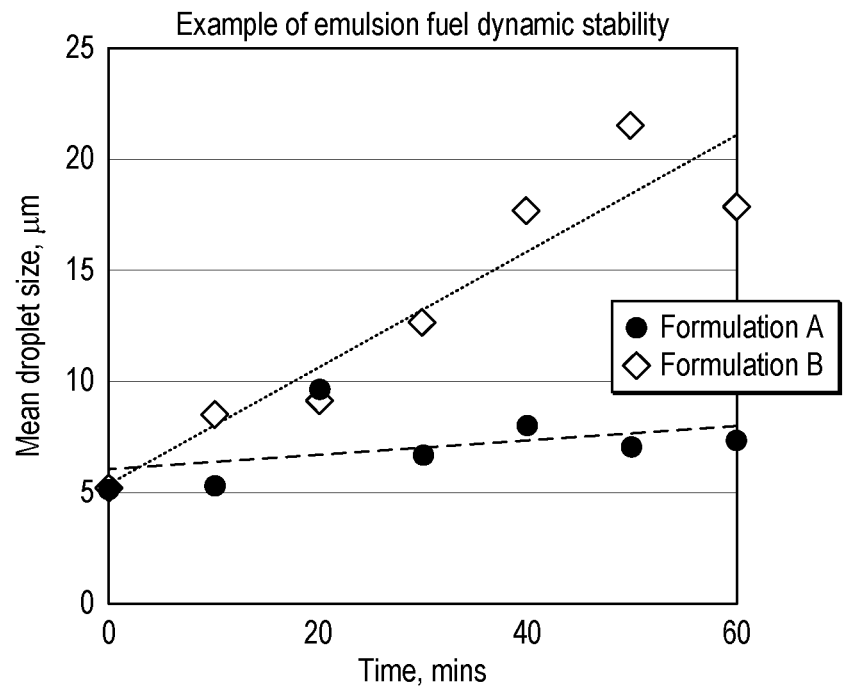
FIG. 16 shows results of dynamic stability from emulsion pump testing.

The rate of change of average droplet size (D[4,3])can be calculated over the period of the test, and the dynamic stability considered acceptable if the rate of change is less than 0.30 µm/min. Examples of the rate of change of average droplet size of emulsion fuel during the dynamic stability pump rig test are given on FIG. 16.

Use of an oil-in-water emulsion fuel, for example one prepared and optimised according to the above process, in full-scale operations demonstrates that conventional equipment for the storage, pumping, heating and transportation of heavy fuel oils can be used, either with no adaption or with only minor adaptions which include:

- using heating mediums such as hot water (less than 80° C.) to maintain the oil-in-water emulsion fuel at a minimum temperature above freezing (e.g., 15° C.) in static storage;
- where possible, modifying pumps to use electrical speed control rather than pressure spill-back control, to minimise exposure of the emulsion fuel to rapid changes in pressure (e.g. pressure differences greater than 20 barg);
- modifying fuel pre-heating systems to use low-pressure, saturated steam (e.g. steam at a pressure of less than 6 barg, such as less than 3 barg), and/or by limiting the heating surfaces to a maximum temperature (less than 125° C.) during flow.

Figure 17:
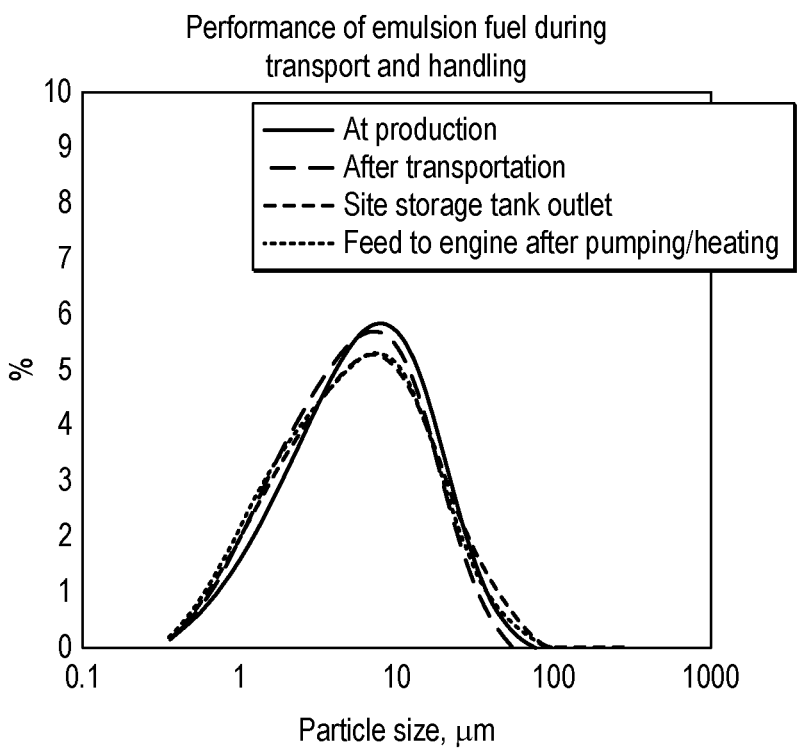
FIG. 17 shows the behaviour of emulsion during transport and handling.

An example of the performance of an emulsion fuel during handling is given in FIG. 17. In this example, details of the droplet size analysis are given for a batch of oil-in-water emulsion fuel at the point of large scale manufacture, after long distance transportation by truck delivery, after a period of storage at location of use, and during operation with final fuel feed system. The data shows the emulsion fuel has a high degree of stability, with very little change in the droplet size distribution taking place.

Pilot Scale Engine Injector Testing

Figure 18:
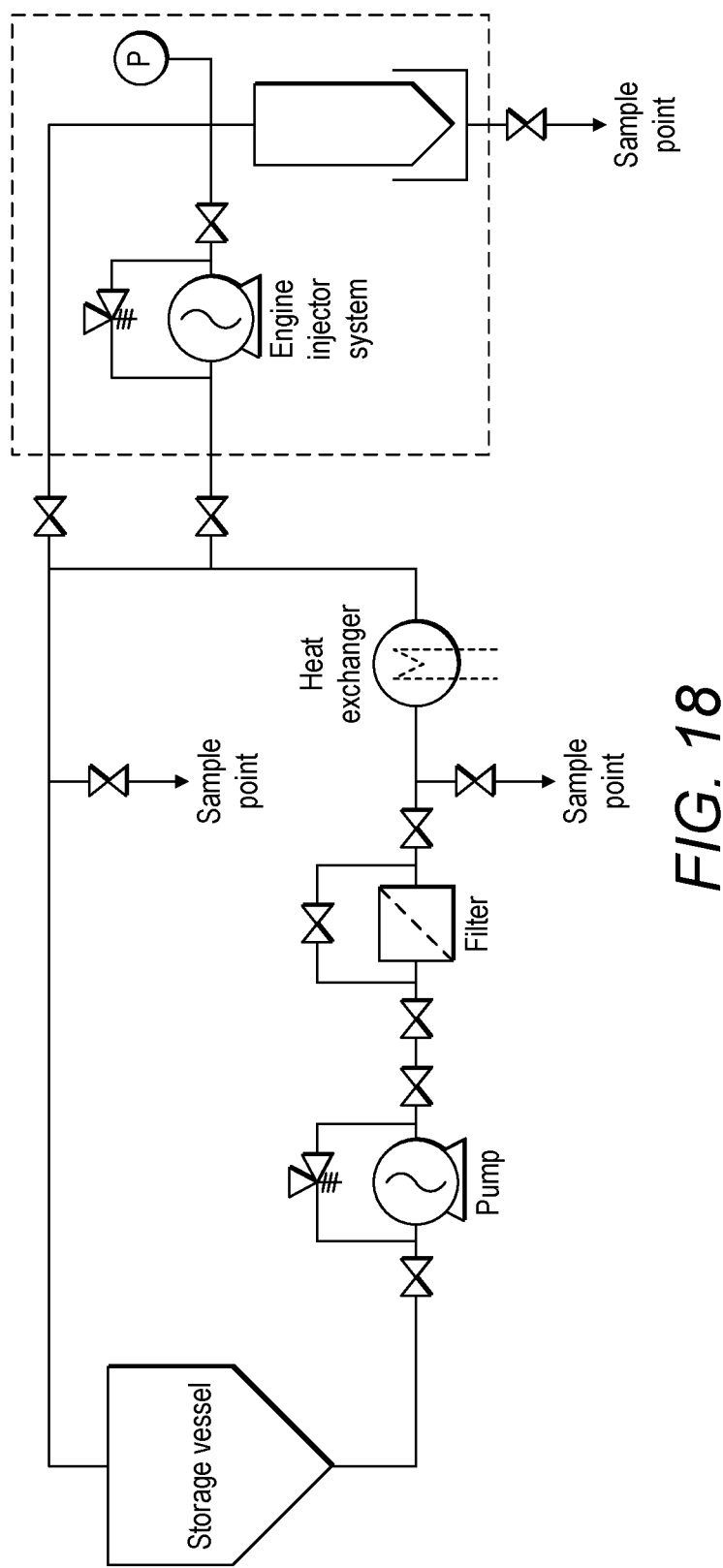
FIG. 18 shows a schematic diagram of an emulsion fuel engine injector test rig.

For this testing, a pilot scale pump testing rig can be used, as shown in FIG. 18. This system is in two main parts, the Injection Rig itself, and a small fuel handling and feed system designed to supply the test emulsion fuel sample at a pre-determined pressure and temperature (e.g. 5-6 bar(g) at 50° C.) for operation of the injector system. This fuel handling system is similar in design to the pilot scale pump test rig as described above.

The main Injection Rig is a self-contained unit and consists of a high pressure pump which is driven by a camshaft linked to an electric motor; the high pressure pump delivers fuel to the injection nozzle at variable feed rates and frequency controlled by a stroke adjustment and variable frequency electrical drive. The unit also includes an electric lubrication oil pump which maintains set pressures within the system.

The candidate emulsion to be tested is pre-heated to the required temperature (normally 50° C.) and then transferred to the pump rig storage vessel. The emulsion is then pumped around the system at a controlled flow rate (300 to 350 kg/h) while the test temperature is maintained. The emulsion is then fed into the full scale engine injector system (which includes the high pressure injector feed pump), and the flow rate through the injector is adjusted as required (reflecting the full operational range of the injector when operated on an engine). Periodic samples are taken for analysis (i.e., droplet size distribution characteristics and viscosity) to measure the impact of the engine injection system. The back-pressure on the injector (typically in the range 300-1500 bar) is also measured to evaluate the hydraulic characteristics of the emulsion fuel formulation being tested.

Figure 19A:
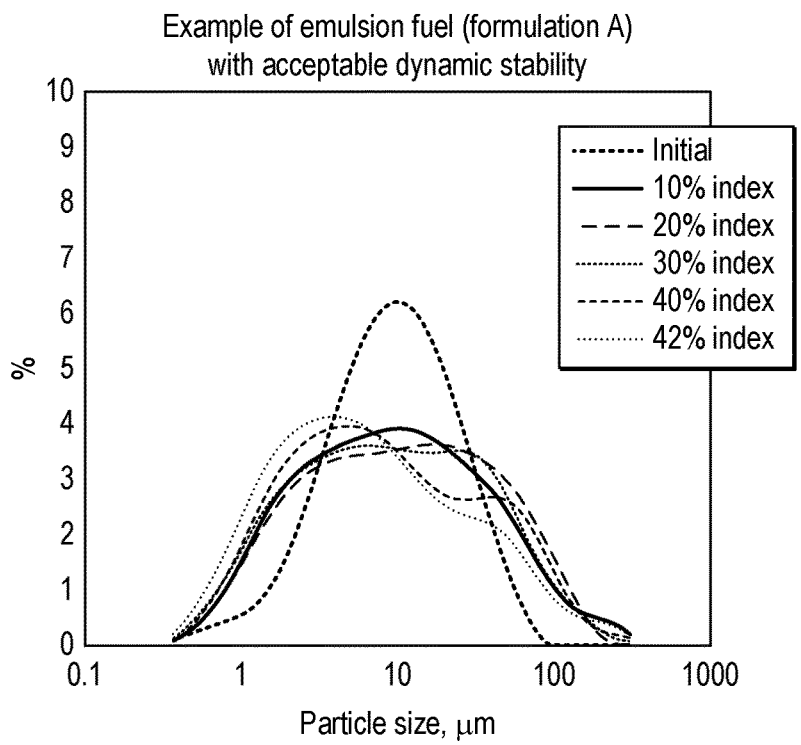
FIGS. 19a and 19b show examples of results from emulsion fuel engine injector testing.
Figure 19B:
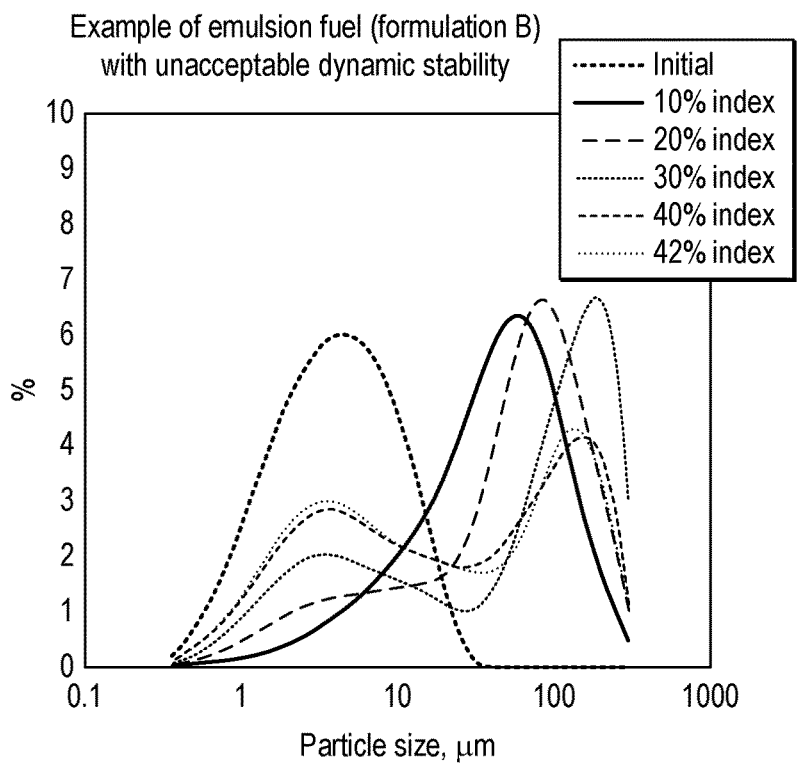

Examples of the results from the dynamic stability injector testing are shown in FIGS. 19a and 19b, (for the same formulations detailed in Table 8). In the tests shown, the %

TABLE 9

Comparison of two formulations

| Parameter | Detail | Formulation A | Formulation B |
|---|---|---|---|
| Primary Surfactant | oleyldiamine ethoxylate, (Armofuel ™ 134) | 0.09% wt | 0.12% wt |
| Secondary Surfactant | ligninamine (5 to 10% in blended solution - Armofuel ™ 143) | 0.5% wt | 0.3% wt |
| Polymeric Stabilising and Flow Improvement Agent | ethylhydroxyethyl cellulose, (Bermocoll EM 7000 FQ) | 0.05% wt | 0.75% wt |
| Acid | Formic Acid | pH 4.5 | pH 4.5 |
| Residue Phase | Urals based Visbreaker residue | Temp = 130° C., 66.9% wt | Temp = 130° C., 67.2% wt |
| Aqueous Phase | Potable Water. | Temp = 50° C. | Temp = 50° C. |
| Mill Operation | DEMINOTECH SEP-0.3R Emulsion Research Plant | 9,000 rpm | 9,000 rpm |
| Droplet Size | Mean (D[4,3]), µm | 5.10 | 5.17 |
| Viscosity | 20 s$^{-1}$ at 50° C. | 112 mPas | 164 mPas | index values refer to the volume setting on the fuel injector, i.e. the volume of fuel injected per injector stroke. The higher the index, the greater the volume of fuel injected, and hence the higher the shear forces and back-pressure.

The dynamic stability is considered acceptable if the emulsion retains a discrete droplet size distribution. As an example, in this specific case for the injector test rig, an acceptable emulsion stability would have less than 3 wt % of droplets above 125 μm, and the distribution would have a relative span of less than 5.0.

In the formulation and manufacture process, specific focus is given to maximising the benefits of the dispersed droplet size characteristics of the hydrocarbon content to optimise the pre-atomised performance of the fuel during its end use. As can be seen in the examples given in FIGS. 15a, 17 and 19a, emulsions as described herein have sufficient inherent stability to be able to retain these optimised characteristics throughout the logistic supply chain to the point of combustion.

The compositions associated with the results displayed in the figures are set out in Table 10 (concentrations in wt %).

TABLE 10

Formulations associated with the figures

| FIG No. | Residue Type | Concentration | Primary Surfactant Type | Concentration |
|---|---|---|---|---|
| 5a & b | North European VBR | 69 | A: quaternary alkyl amine | 0.3 |
|  | North European VBR | 69 | B: tallowtripropylenetetramine | 0.3 |
|  | North European VBR | 69 | C: alkylpropylenediamine | 0.3 |
|  | North European VBR | 69 | D: oleyldiamine ethoxylate | 0.3 |
| 6 | North European VBR | 70 | oleyldiamine ethoxylate | 0.09 |
| 7a & b | Scandanavian VR | 70 | oleyldiamine ethoxylate | 0.09 |
| 8 | Urals VFVBR | 70 | oleyldiamine ethoxylate | 0.3 |
| 9 | North European VBR | 70 | oleyldiamine ethoxylate | 0.09 |
| 10a & b | Urals VBR | 70.5 | oleyldiamine ethoxylate | 0.3 |
| 11 | Urals VBR | 70.5 | oleyldiamine ethoxylate | 0.3 |
| 12 | Urals VBR | 65-70 | oleyldiamine ethoxylate | 0.12 |
| 13 | Urals VFVBR | 67 | A: alkylpropylenediamine | 0.3 |
|  | Urals VFVBR | 67 | B: oleyldiamine ethoxylate | 0.3 |
| 15a & b | Urals VBR | 65 | A: oleyldiamine ethoxylate | 0.09 |
|  | Urals VBR | 65 | B: oleyldiamine ethoxylate | 0.12 |
| 16 | Urals VBR | 65 | A: oleyldiamine ethoxylate | 0.09 |
|  | Urals VBR | 65 | B: oleyldiamine ethoxylate | 0.12 |
| 17 | Urals VBR | 70 | A: oleyldiamine ethoxylate | 0.09 |
| 19a | Urals VBR | 70 | oleyldiamine ethoxylate | 0.12 |
| 19b | Urals VBR | 70 | oleyldiamine ethoxylate | 0.12 |

| FIG No. | Secondary Surfactant Type | Concentration | Polymeric Stabiliser Type | Concentration |
|---|---|---|---|---|
| 5a & b | none | 0 | none | 0 |
|  | none | 0 | none | 0 |
|  | none | 0 | none | 0 |
|  | none | 0 | none | 0 |
| 6 | ligninamine | 0.5 | ethylhydroxyethyl cellulose | 0.03 |
| 7a & b | ligninamine | 0.5 | ethylhydroxyethyl cellulose | 0-0.5 |
| 8 | none | 0 | ethylhydroxyethyl cellulose | 0.03 |
| 9 | ligninamine | 0.5 | ethylhydroxyethyl cellulose | 0.02 |
| 10a & b | none | 0 | none | 0 |
| 11 | none | 0 | none | 0 |
| 12 | ligninamine | 0.6 | ethylhydroxyethyl cellulose | 0.05 |
| 13 | none | 0 | ethylhydroxyethyl cellulose | 0.05 |
|  | none | 0 | ethylhydroxyethyl cellulose | 0.05 |
| 15a & b | A ligninamine | 0.5 | ethylhydroxyethyl cellulose | 0.05 |
|  | B ligninamine | 0.3 | ethylhydroxyethyl cellulose | 0.075 |
| 16 | A ligninamine | 0.5 | ethylhydroxyethyl cellulose | 0.05 |
|  | B ligninamine | 0.3 | ethylhydroxyethyl cellulose | 0.075 |
| 17 | ligninamine | 0.5 | ethylhydroxyethyl cellulose | 0.03 |
| 19a | ligninamine | 0.6 | ethylhydroxyethyl cellulose | 0.075 |
| 19b | ligninamine | 0.3 | ethylhydroxyethyl cellulose | 0.05 |

| FIG No. | Acid Type | pH (of aqueous phase) |
|---|---|---|
| 5a & b | formic | 4.5 |
|  | formic | 4.5 |
|  | formic | 4.5 |
|  | formic | 4.5 |
| 6 | formic | 3.0-4.5 |
| 7a & b | formic | 4.5 |
| 8 | formic | 4 |
| 9 | formic | 4.5 |
| 10a & b | formic | 4.5 |
| 11 | formic | 4.5 |
| 12 | formic | 4.5 |
| 13 | formic | 4 |
|  | formic | 4 |
| 15a & b | formic | 4.5 |
|  | formic | 4.5 |
| 16 | formic | 4.5 |
|  | formic | 4.5 |

TABLE 10-continued

| Formulations associated with the figures | | |
|---|---|---|
| 17 | formic | 4.5 |
| 19a | formic | 4.5 |
| 19b | formic | 4.5 |

The invention claimed is:

1. An oil-in-water emulsion for use as a fuel comprising an oil phase and an aqueous phase, at least one primary surfactant selected from the group consisting of fatty alkyl amines, ethoxylated fatty alkylamines, ethoxylated fatty alkyl monoamines, methylated fatty alkyl monoamines, methylated fatty alkyl amines, and quaternary fatty alkyl amines; greater than 0.3 and up to 2.0 wt % of secondary surfactant selected from one or more lignin amines; and one or more organic acids; wherein the oil phase is dispersed in the aqueous phase, and wherein the oil-in-water emulsion has the following characteristics:
an average droplet size (D[4,3]) in the range of from 3 to 15 μm, wherein the average droplet size is expressed as the Volume Moment Mean and is measured using light scattering techniques;
less than 3 wt % of the droplets have a particle size of greater than 125 μm, wherein droplet size is measured using light scattering techniques; and
a viscosity of greater than 100 and up to 700 mPas at 50° C.±10% and 20 s$^{-1}$±10%, wherein viscosity is measured on a Malvern Kinexus™ instrument.

2. The oil-in-water emulsion according to claim 1, comprising from 0.05 to 0.6 wt % primary surfactant.

3. The oil-in-water emulsion according to claim 1, comprising in the range of from greater than 0.3 and up to 0.7 wt % of secondary surfactant.

4. The oil-in-water emulsion according to claim 1, in which the oil of the oil-phase is a hydrocarbon-containing oil having a viscosity of up to 300 000 cSt at 100° C.

5. The oil-in-water emulsion according to claim 1, in which the oil of the oil-phase is a hydrocarbon-containing oil having a viscosity of at least 200 cSt at 100° C.

6. The oil-in-water emulsion according to claim 1, in which the oil of the oil-phase is a hydrocarbon residue derived from one or more of: processed heavy crude oil or natural bitumen; refinery atmospheric distillation; refinery vacuum distillation; refinery visbreaking, thermal cracking or steam cracking; refinery cat-cracking; refinery hydroprocessing and hydrocracking; and de-asphalting processes.

7. The oil-in-water emulsion according to claim 1, in which the hydrocarbon is a hydrocarbon residue selected from those having Chemical Abstracts Service (CAS) Registry Numbers 8052-42-4, 64741-45-3, 64741-56-6, 64741-67-9, 64741-75-9, 64741-80-6, 64742-07-0, 64742-78-5, 64742-85-4, 68748-13-7, 68783-13-1, 70913-85-8, 91995-23-2 or 92062-05-0.

8. The oil-in-water emulsion according to claim 1, additionally comprising one or more polymeric stabilisers, at least one of which is selected from the group consisting of alkyl hydroxyalkyl cellulose ethers, guar gum, starch and starch derivatives, hydroxyethyl cellulose and ethyl hydroxyl ethyl cellulose.

9. The oil-in-water emulsion according to claim 1, comprising up to 0.25 wt % polymeric stabiliser and flow improving agents.

10. The oil-in-water emulsion according to claim 1, comprising 0.03 to 0.08 wt % polymeric stabiliser and flow improving agents.

11. The oil-in-water emulsion according to claim 1, in which at least one of the one or more organic acids is selected from methanesulfonic acid and formic acid.

12. A marine fuel composition comprising the oil-in-water emulsion of claim 1.

13. A marine fuel composition consisting of the oil-in-water emulsion of claim 1.

14. A process for preparing an oil-in-water emulsion as defined in claim 1, comprising preparing an aqueous phase comprising a primary surfactant, heating a hydrocarbon-containing oil-phase, and blending the hydrocarbon-containing oil-phase and the aqueous phase under conditions sufficient to form an oil-in-water emulsion.

* * * * *